(12) United States Patent
Kobayashi

(10) Patent No.: US 11,389,215 B2
(45) Date of Patent: Jul. 19, 2022

(54) BONE FIXATION SYSTEM INCLUDING COMPRESSION PLATE

(71) Applicant: DePuy Synthes Products, Inc., Raynham, MA (US)

(72) Inventor: Kenneth Kobayashi, Exton, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 301 days.

(21) Appl. No.: 16/161,149

(22) Filed: Oct. 16, 2018

(65) Prior Publication Data
US 2019/0110824 A1 Apr. 18, 2019

Related U.S. Application Data

(60) Provisional application No. 62/573,786, filed on Oct. 18, 2017.

(51) Int. Cl.
A61B 17/80 (2006.01)
A61B 17/86 (2006.01)
A61B 17/88 (2006.01)
A61B 17/00 (2006.01)
A61B 17/68 (2006.01)
A61B 17/90 (2006.01)

(52) U.S. Cl.
CPC ...... A61B 17/8014 (2013.01); A61B 17/8019 (2013.01); A61B 17/8061 (2013.01); A61B 17/8085 (2013.01); A61B 17/8625 (2013.01); A61B 17/88 (2013.01); A61B 17/90 (2021.08); A61B 2017/00862 (2013.01); A61B 2017/00867 (2013.01); A61B 2017/681 (2013.01)

(58) Field of Classification Search
CPC .................. A61B 17/8004; A61B 17/8085
See application file for complete search history.

(56) References Cited

U.S. PATENT DOCUMENTS

| 5,201,737 A | * | 4/1993 | Leibinger | A61B 17/688 606/280 |
|---|---|---|---|---|
| 5,752,958 A | | 5/1998 | Wellisz | |
| 6,071,291 A | | 6/2000 | Forst et al. | |
| 9,149,316 B2 | | 10/2015 | Appenzeller et al. | |
| 9,517,097 B2 | | 12/2016 | Rise et al. | |
| 2003/0100898 A1 | | 5/2003 | Wellisz | |

(Continued)

FOREIGN PATENT DOCUMENTS

| EP | 1957128 | 8/2008 |
|---|---|---|
| EP | 2680772 | 1/2014 |

(Continued)

Primary Examiner — Nicholas W Woodall
(74) Attorney, Agent, or Firm — BakerHostetler

(57) ABSTRACT

A bone plate is provided that is configured to provide compression to comminuted bone fragments, so as to reduce the respective bone gaps and promote healing. The bone plate can be moved from a first position to a loaded position, and placed against bone in the loaded position. The bone plate can then be secured to underlying bone. The bone plate then moves to an intermediate compression position that compresses bone fragments of a comminuted bone fracture together. An insertion instrument is also described that can be used to place the bone plate against the underlying bone, and guide insertion of a bone anchor to secure the bone plate to the underlying bone.

19 Claims, 11 Drawing Sheets

(56) References Cited

U.S. PATENT DOCUMENTS

| | | |
|---|---|---|
| 2004/0172040 A1* | 9/2004 | Heggeness ......... A61B 17/8869 606/105 |
| 2005/0149032 A1 | 7/2005 | Vaughen et al. |
| 2005/0216008 A1 | 9/2005 | Zwirnmann et al. |
| 2005/0261780 A1 | 11/2005 | Heino et al. |
| 2009/0018587 A1 | 1/2009 | Bottlang |
| 2010/0312286 A1 | 12/2010 | Dell Oca |
| 2013/0079832 A1 | 3/2013 | Bottlang |
| 2014/0243904 A1 | 8/2014 | Miller |
| 2015/0230843 A1* | 8/2015 | Palmer ............... A61B 17/8875 606/331 |
| 2016/0235451 A1* | 8/2016 | Johnston, Jr. ........ A61B 17/808 |

FOREIGN PATENT DOCUMENTS

| | | |
|---|---|---|
| WO | 2007/142743 A2 | 12/2007 |
| WO | 2009/039430 A1 | 3/2009 |
| WO | 2012/116819 A1 | 9/2012 |

\* cited by examiner

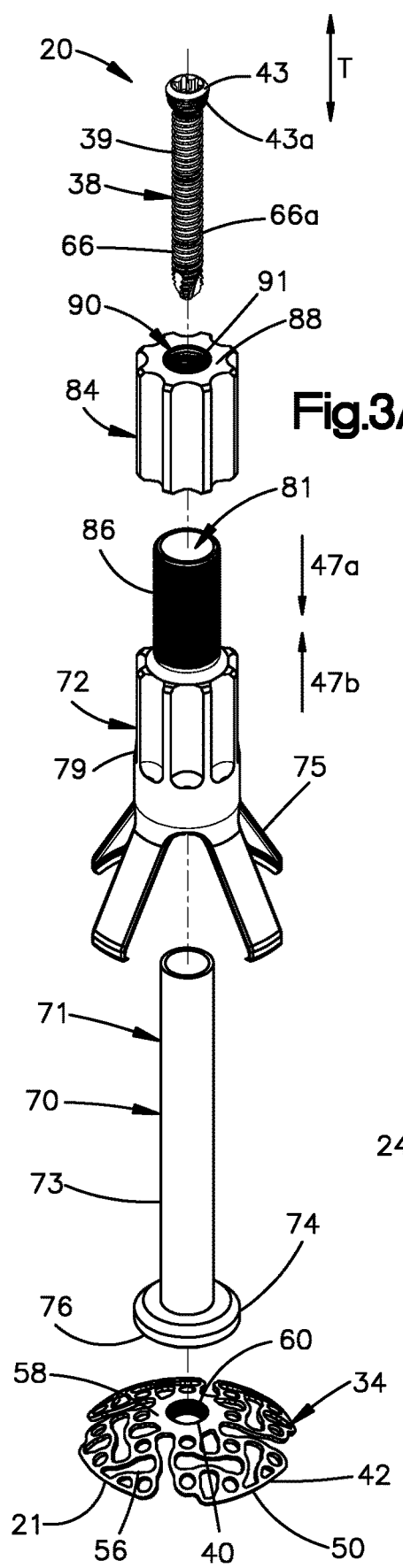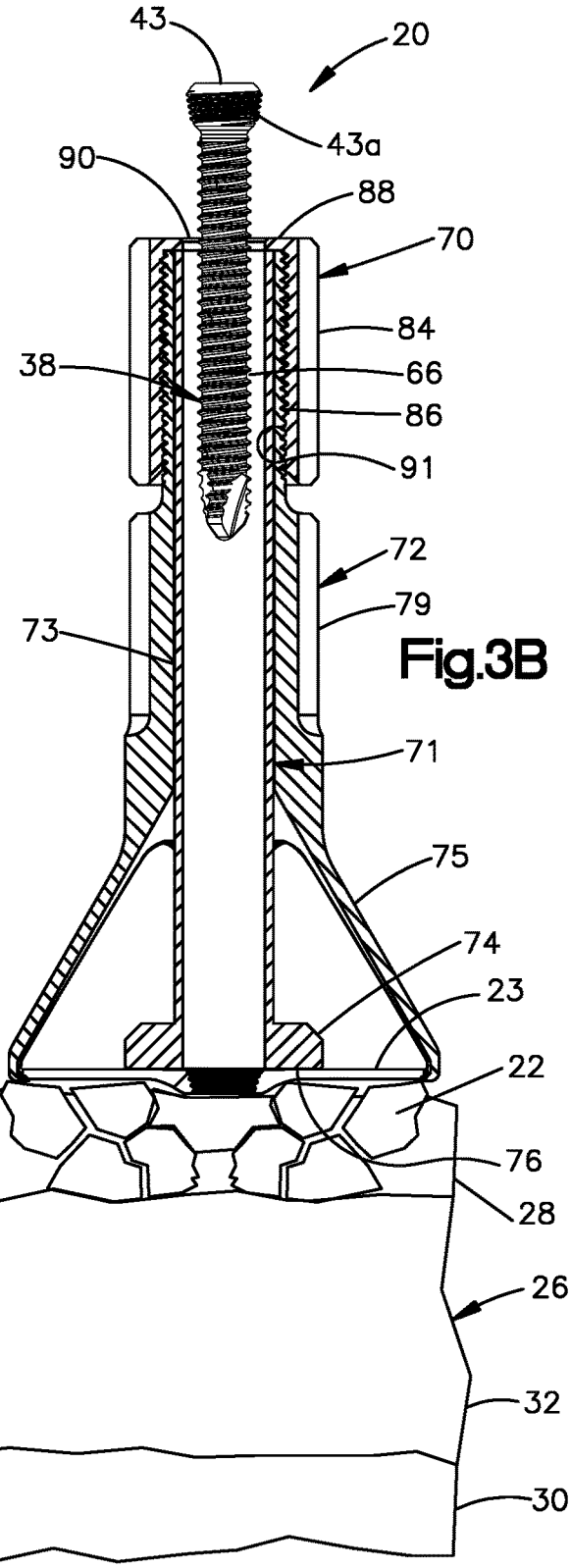

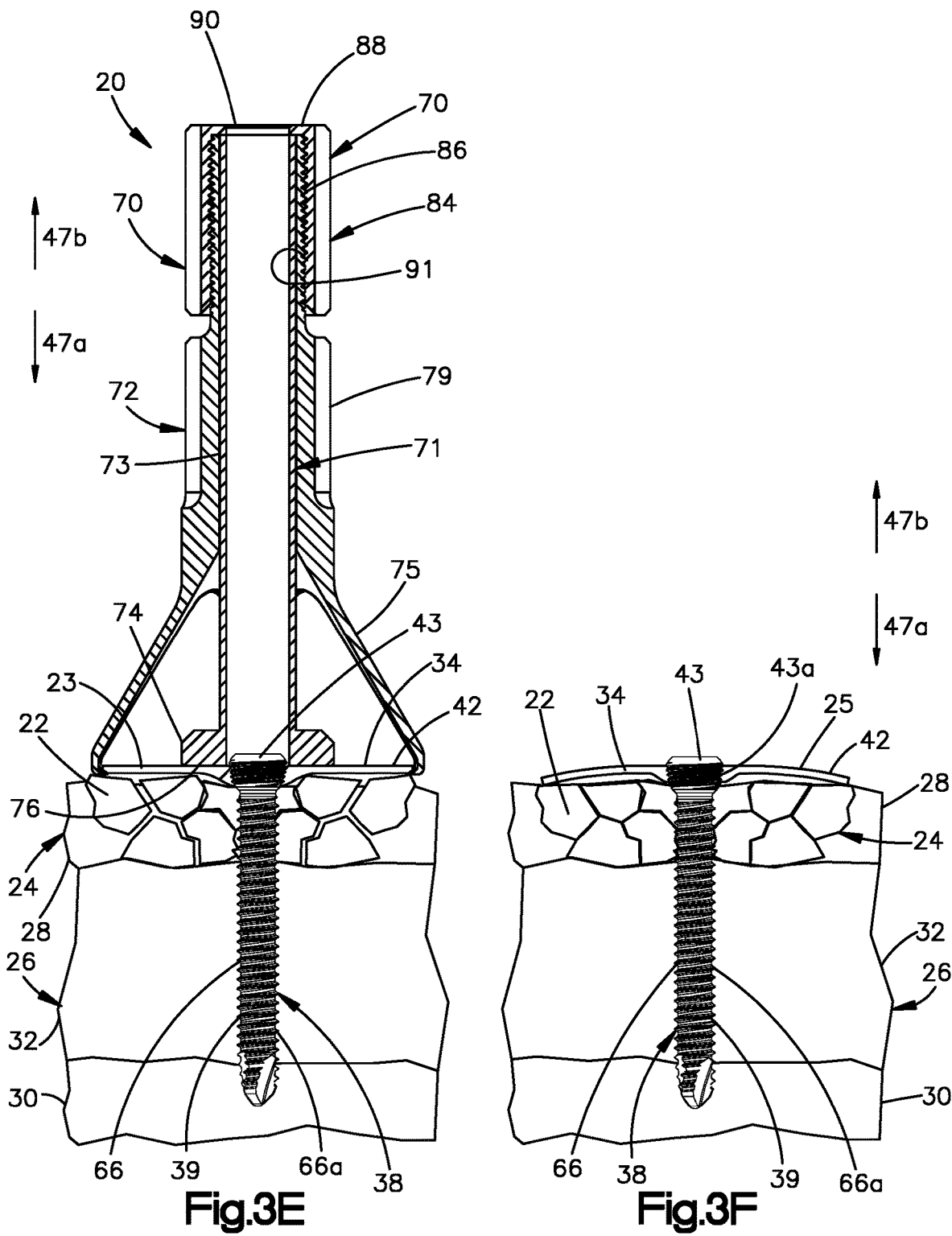

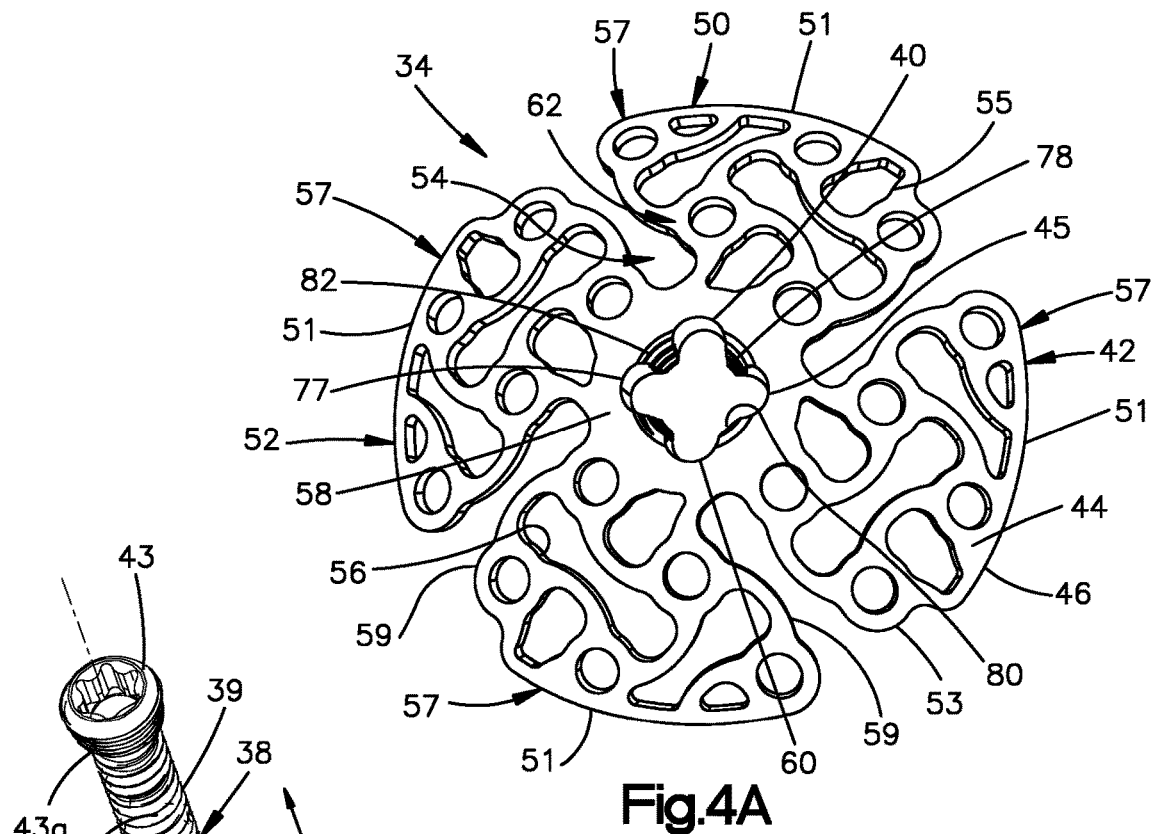
Fig.4A
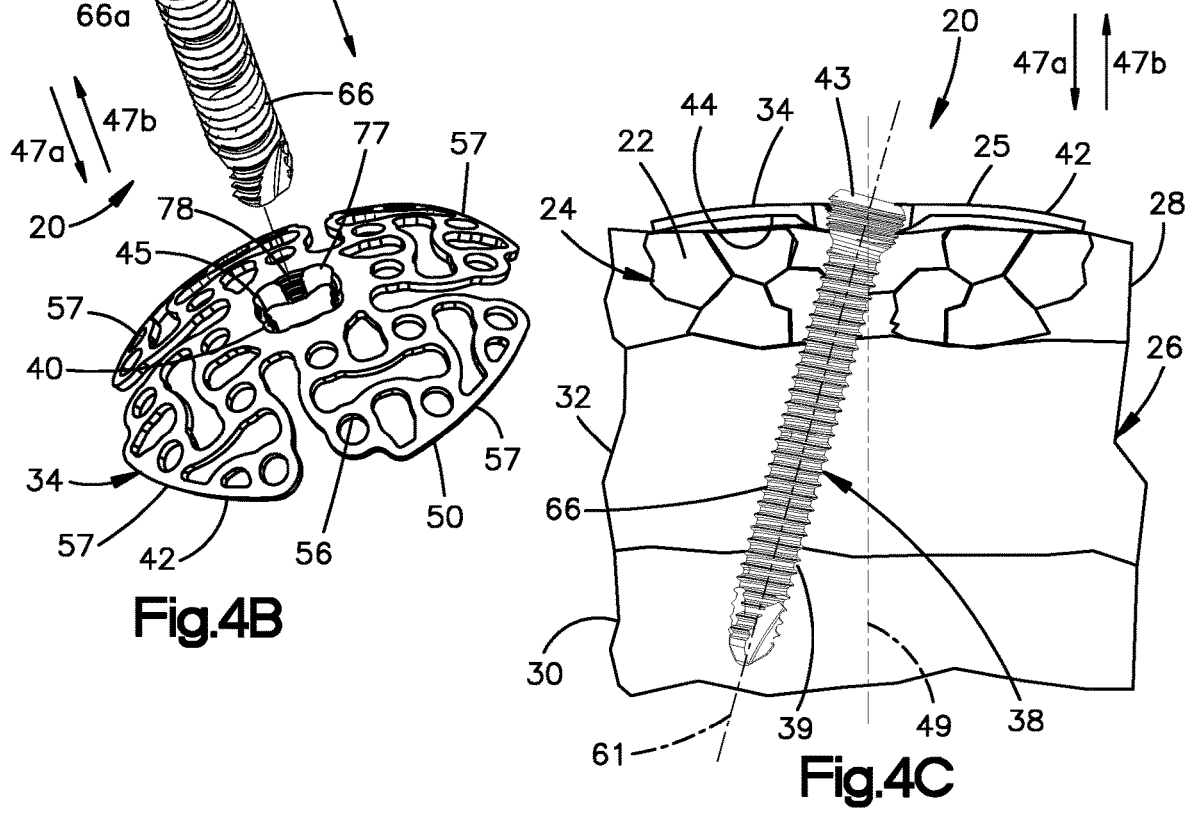
Fig.4B
Fig.4C

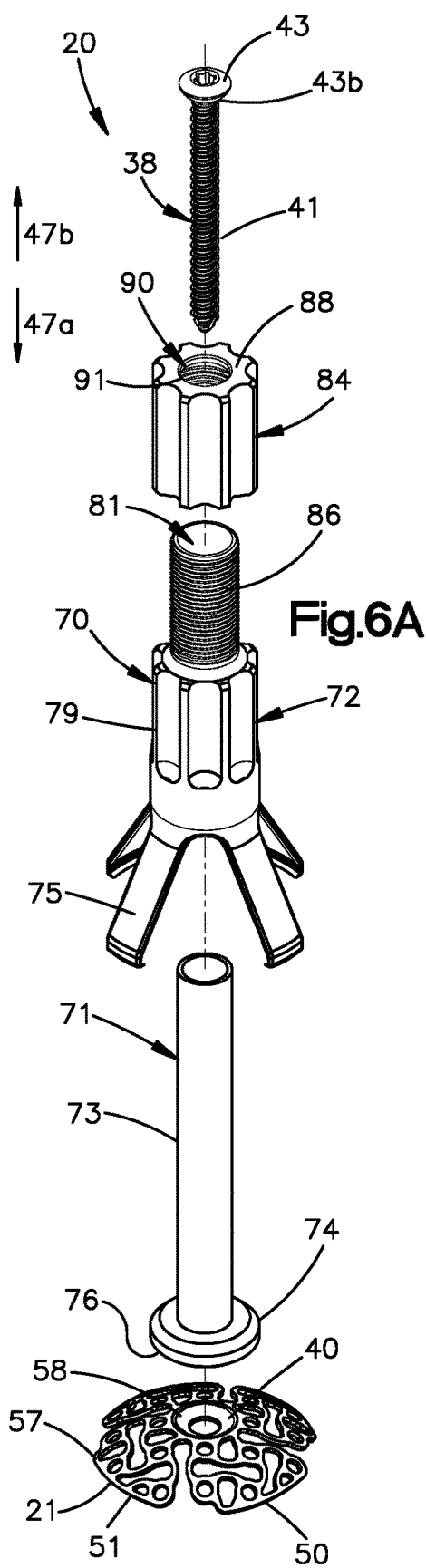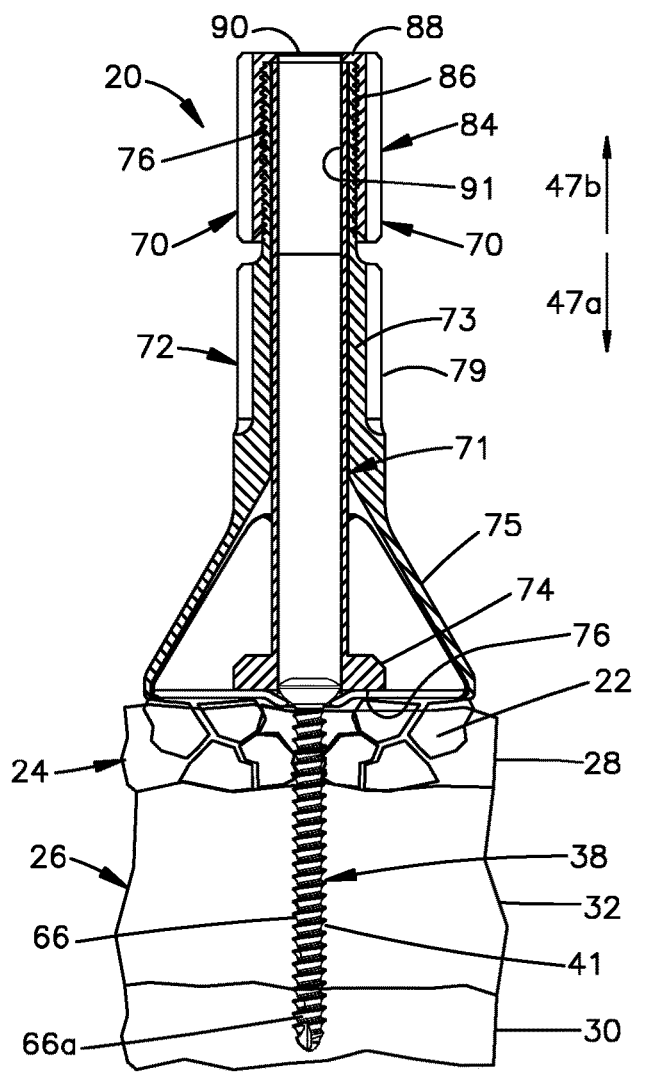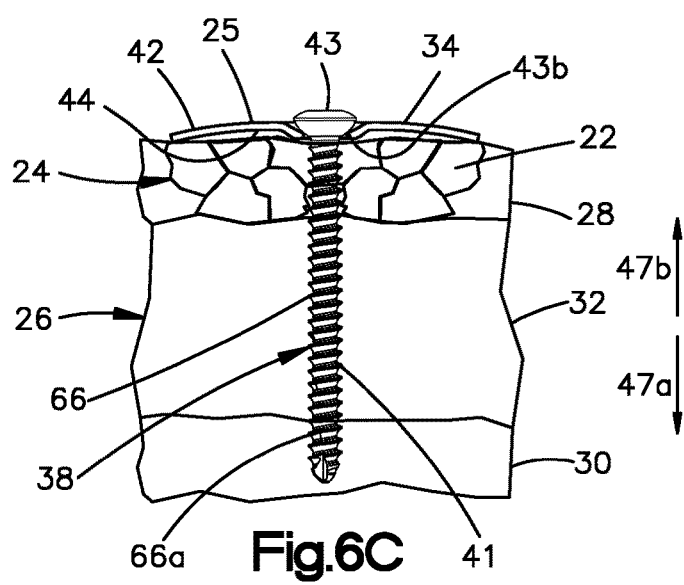

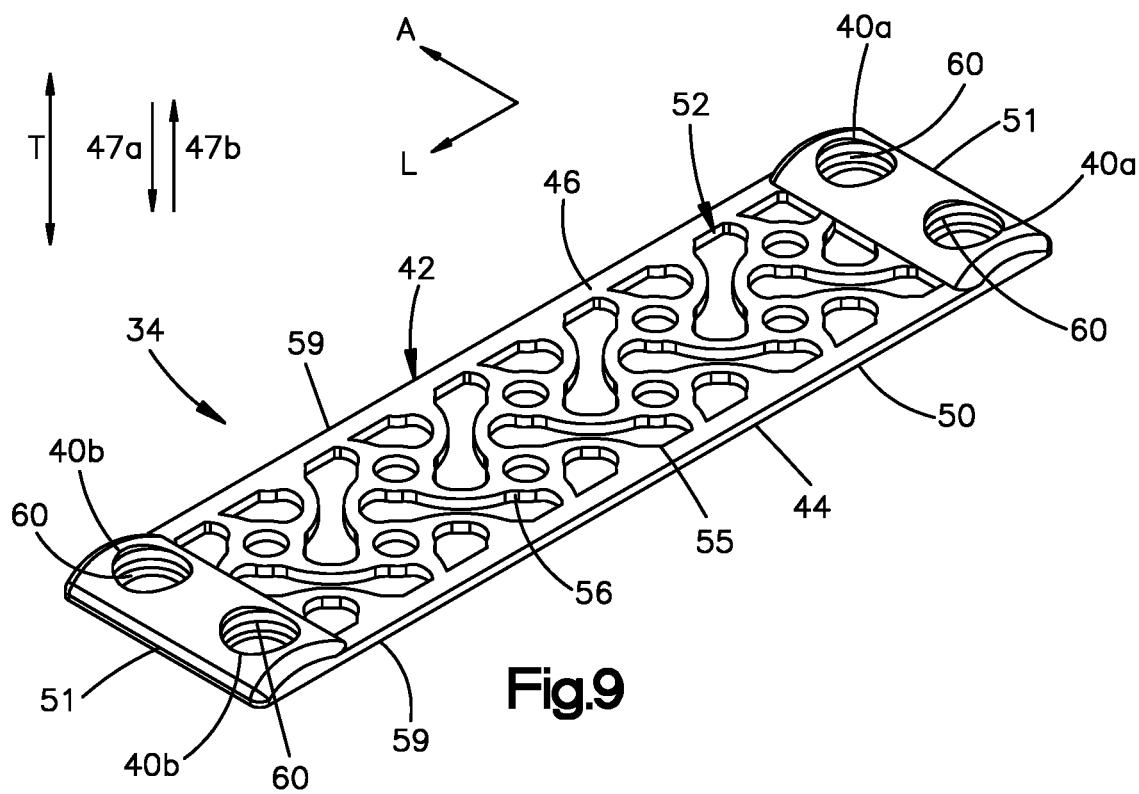
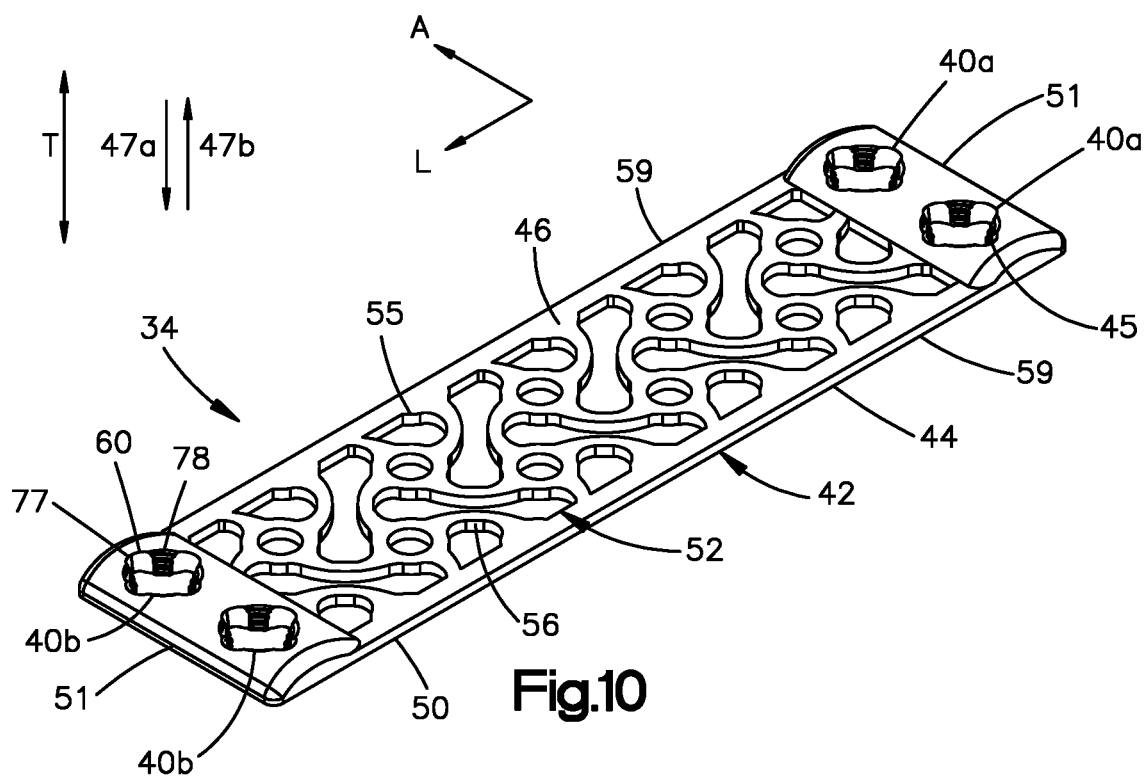

BONE FIXATION SYSTEM INCLUDING COMPRESSION PLATE

CROSS-REFERENCE TO RELATED APPLICATIONS

This claims priority to U.S. Provisional Patent Application Ser. No. 62/573,786 filed Oct. 18, 2017, the disclosure of which is hereby incorporated by reference as if set forth in its entirety herein.

FIELD OF THE INVENTION

This disclosure relates generally to bone fixation, and in particular relates to a bone fixation system provides compression to enhance the stabilization of bone fractures.

BACKGROUND OF THE INVENTION

Many types of bone fixation systems are conventionally available to stabilize bone fragments following bone fractures to promote bone healing. Bone fixation systems typically include a bone plate that is placed against the bone across the fracture location. Bone anchors, typically configured as bone screws, are driven through bone fixation holes of the bone plate and into the respective underlying bone fragments. The bone fragments are thus stabilized with respect to the bone plate and each other. The bone fragments can be compressed toward each other prior so as to reduce the fracture prior to fixation of the bone anchors.

Bone screws are conventionally available as locking screws or non-locking screws (also known as compression screws). Locking screws are configured to lock to the bone plate. For instance, locking screws typically can be externally threaded at the screw head, and the bone plate typically includes threading in the fixation hole. The locking screw is inserted through the fixation hole of the bone plate, and rotated so as to gain purchase with the underlying bone as it is driven into the bone. The locking screw is rotated until the screw head is inserted into the fixation hole, at which point the threading of the screw head purchases with the threading in the fixation hole. Thus, the locking screw is locked to the bone plate, thereby preventing backout of the bone screw.

Alternatively, the bone screws can be configured to compress the bone plate against the underlying bone. In particular, the external surface of the bone screw can be unthreaded. Accordingly, the bone screw is driven into the underlying bone until the screw head bears against the bone plate (typically in the fixation hole). Continued rotation of the bone screw causes the screw head to compress the bone plate against the underlying bone. This can be useful when it is desired to compress two or more bone fragments against each other to promote bone healing. Unfortunately, conventional locking screws are not also configured to cause compression of the bone plate against the underlying bone.

Unfortunately, many high energy fractures produce highly comminuted fractures that are not easily addressed with conventional bone plating techniques. In particular, the small bone fragments associated with highly comminuted fractures are too small to receive bone screws. As a result, these bone fragments are often left untreated.

It is therefore desirable to provide a bone plate that is configured to stabilize highly comminuted bone fractures.

BRIEF SUMMARY OF THE INVENTION

The following Summary is provided to introduce a selection of concepts in a simplified form that are further described below in the Detailed Description of Illustrative Embodiments. This Summary is not intended to identify key features or essential features of the invention, nor is it intended to be used to limit the scope of the invention. Reference is made to the claims for that purpose.

In accordance with one aspect of the present disclosure, a bone plate can include a bone plate body that defines an outer surface and a bone facing surface opposite the outer surface in an inward direction. The bone plate further includes a bone screw hole that extends through the bone plate body from the outer surface to the bone facing surface. The bone plate can be movable from a first position to a loaded position, and the bone plate is further biased to iterate from the loaded position toward the first position. When the bone plate is in a compression position between the first position and the loaded position, the bone plate is configured to apply a compressive forced against an underlying bone.

Additional features and advantages will be made apparent from the following detailed description of illustrative embodiments with reference to the accompanying drawings.

BRIEF DESCRIPTION OF THE SEVERAL VIEWS OF THE DRAWINGS

The foregoing summary, as well as the following detailed description, is better understood when read in conjunction with the appended drawings. There is shown in the drawings example embodiments, in which like reference numerals correspond to like reference numerals throughout. The present disclosure is not limited to the specific embodiments and methods disclosed, and reference is made to the claims for that purpose.

FIG. 3A is a perspective view of the bone fixation system illustrated in FIG. 1A, further including an insertion instrument;

FIG. 3B is a sectional side elevation view of the bone fixation system illustrated in FIG. 3C, but showing the insertion instrument having caused the bone plate to move from the first position to the loaded position;

FIG. 3E is a sectional side elevation view of the bone fixation system illustrated in FIG. 3D, but showing the bone fixation member attached to the bone plate and the underlying bone while the bone plate is in the loaded position;

FIG. 3F is a sectional side elevation view of the bone fixation system illustrated in FIG. 3E, but with the insertion instrument removed and the bone plate having moved from the loaded position to a compression position;

FIG. 4A is a perspective view of the bone plate similar to FIG. 2A, but including a variable-angle locking hole in accordance with another embodiment;

FIG. 4B is an exploded perspective view of the bone fixation system illustrated in FIG. 4A, showing the bone fixation member aligned to be inserted into a bone fixation hole of the bone plate;

FIG. 4C is a sectional side elevation view of the bone fixation system illustrated in FIG. 4B, showing the bone fixation member attached to the bone plate and the underlying bone;

FIG. 6A is an exploded view of the bone fixation system illustrated in FIG. 5A, further including the insertion instrument as illustrated in FIG. 3A, and showing the bone plate in the first position;

FIG. 6B is a sectional side elevation view of the bone fixation system illustrated in FIG. 3C, but showing the bone fixation member compressing the bone plate against the underlying bone and causing the bone plate to move from the first position to the loaded position;

FIG. 6C is a sectional side elevation view of the bone fixation system illustrated in FIG. 6B, but with the insertion instrument removed and the bone plate having moved from the loaded position to a compression position;

FIG. 9 is a perspective view of the bone plate illustrated in FIG. 8A, but including threaded bone fixation holes in accordance with another embodiment; and FIG. 10 is a perspective view of the bone plate illustrated in FIG. 8A, but including variable-angle locking holes in accordance with another embodiment.

DETAILED DESCRIPTION OF THE INVENTION

Figure 1A:
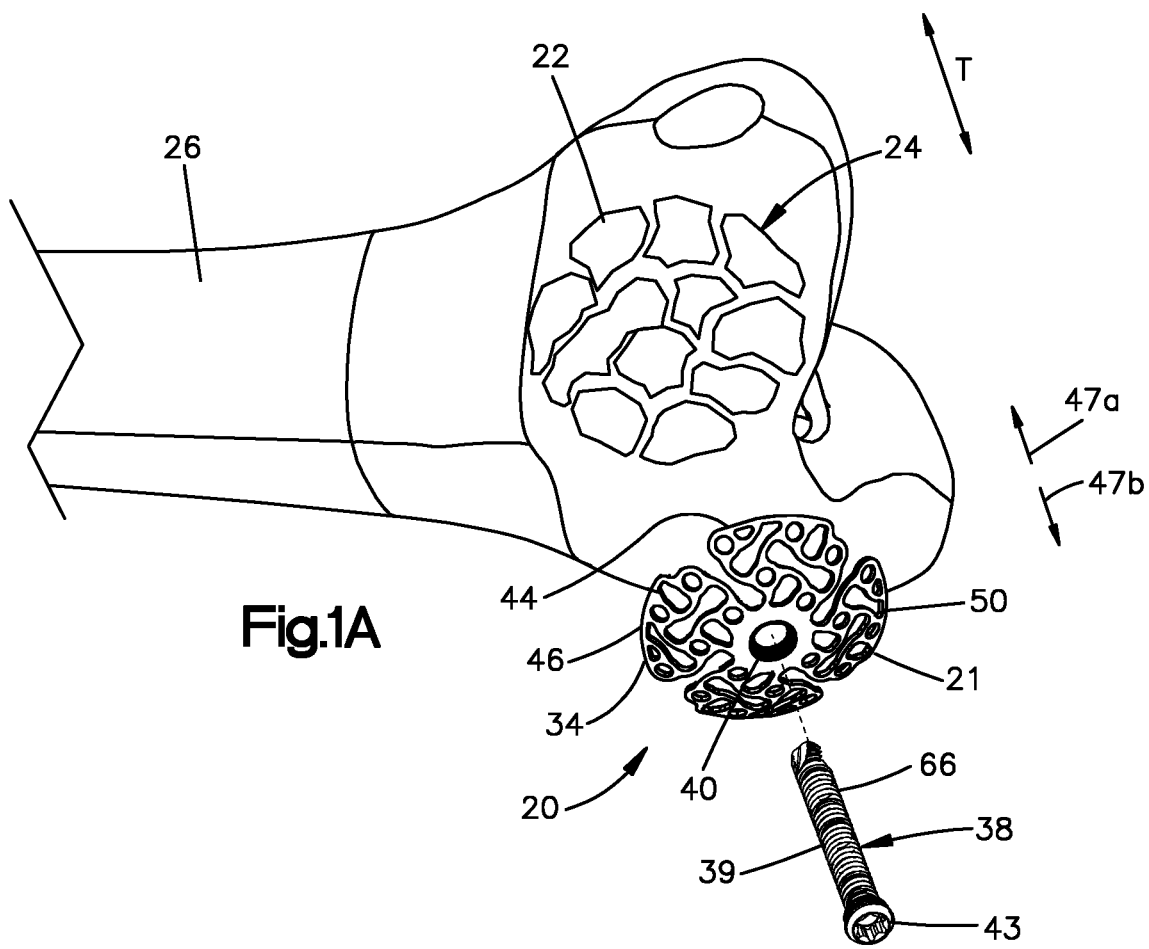
FIG. 1A is an exploded perspective view of a bone fixation system including a bone plate and a bone fixation member configured to attach the bone plate to an underlying fractured bone.
Figure 1B:
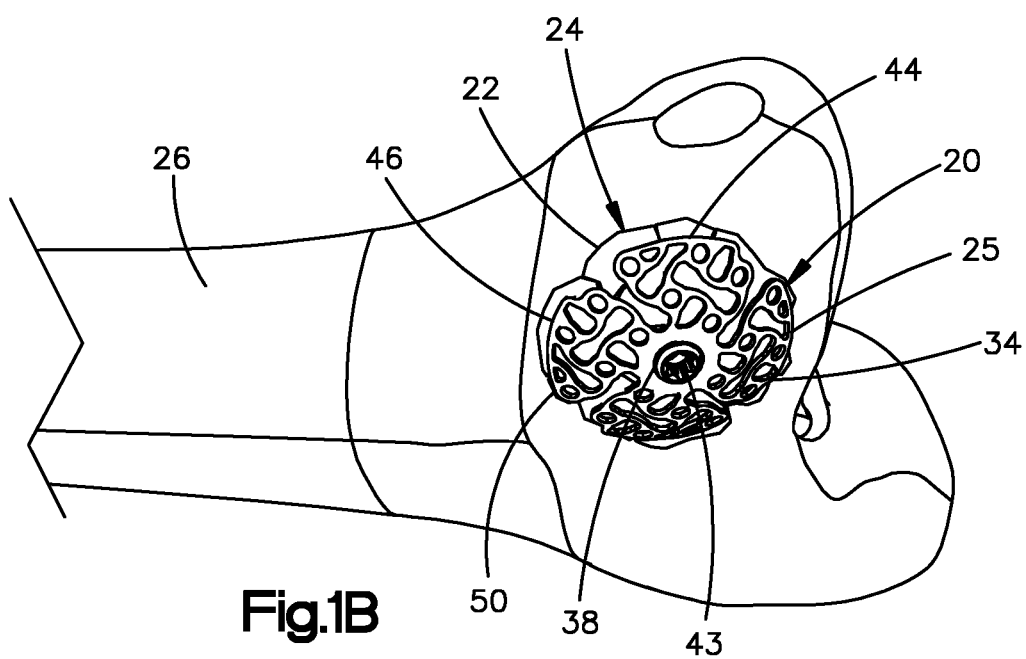
FIG. 1B is a perspective view of the bone fixation system illustrated in FIG. 1A, showing the bone plate attached to the underlying fractured bone.

Referring to FIGS. 1A-1B, a bone fixation system 20 is configured to cause bone fragments 22 of a comminuted bone fracture 24 to compress against each other to promote healing. Thus, an anatomical bone 26 is illustrated as including a first or near cortical wall 28, a second or far cortical wall 30 (see FIG. 3F) opposite the near cortical wall 28, and a cancellous bone portion 32 disposed between the near cortical wall 28 and the far cortical wall 30. As illustrated, the bone 26 has undergone the comminuted fracture 24 that has produced the plurality of comminuted bone fragments 22 at the near cortical wall 28. The bone 26 can be a human bone or a bone of a quadruped. Further, it should be appreciated that the bone 26 can be any suitable anatomical bone that is subject to highly comminuted fractures of the type that are not easily addressed using standard plating techniques. By way of example, the bone 26 can be a tibia (such as a distal tibia or proximal tibia), a femur, humerus, ulna, bones of the hand, or bones of the foot.

As will be appreciated from the description below, the bone fixation system 20 can include a bone plate 34 that is configured to apply a compressive force to at least some of the bone fragments 22 that causes the bone fragments 22 to compress toward each other, thereby promoting bone healing. In particular, the bone plate 34 is configured to iterate from a first position 21 as illustrated in FIG. 1A to a loaded position 23 shown in FIG. 3D. The bone plate 34 can be resilient, such that the first position 21 is a natural, or relaxed, position of the bone plate 34, and the loaded position 23 is a flexed position of the bone plate 34. Alternatively, if desired the first position 21 can be a pre-loaded position that is flexed with respect to the natural position, but not as flexed as the loaded position 23. The bone plate 34 can be moved to the loaded position 23 using one of many available methods and apparatus, as is described in more detail below.

Because the bone plate 34 can be resilient, when the bone plate is released from the loaded position 23, the bone plate moves from the loaded position 23 to a compression position 25 in which the bone plate 34 applies a compression force to the underlying bone fragments 22, as illustrated in FIG. 1B. Because the bone plate 34 is biased to return to the first position 21 from the loaded position 23, the bone plate 34 is flexed less in the compression position 25 than when in the loaded position 23. It can still be said that the bone plate 34 can be flexed when in the compression position. In one example, the bone plate 34 can be flatter in the loaded position 23 than when in each of the first position 21 and the compression position 25. The bone plate 34 can be flatter in the compression position 25 than in the first position 21. In this regard, it should be appreciated that the bone plate 34 has a length along a direction perpendicular to the transverse direction T that is greater when the bone plate is in the loaded position 23 than when the bone plate is in the first position 21. Further, the length of the bone plate 34 can be greater in the compression position 25 than in the first position 21. The length of the bone plate 34 in the compression position 25 can be less than when the bone plate 34 is in the loaded position 23.

The bone plate 34 can be disposed against the underlying bone 26 when the bone plate is in the loaded position 23, such that the bone plate 34 applies the compressive force to the bone fragments 22 when it iterates from the loaded position 23 to the compression position 25. In particular, the bone plate 34 can be placed against the near cortical wall 28.

The bone fixation system 20 can further include at least one bone fixation member 38. The bone fixation member 38 can be configured as a bone screw that is configured to be inserted into a bone fixation hole 40 of the bone plate 34 so as to threadedly purchase with the underlying bone 26.

When the bone fixation member 38 is configured as the bone screw, the bone fixation hole 40 can be referred to as a bone screw hole. The bone fixation member 38 can thus extend through the bone fixation hole 40, through the near cortical wall 28, through the cancellous bone portion 32, and into the far cortical wall 30. Because the bone fixation member 38 can pass through the bone fragments 22 at the near cortical wall 28, the bone fixation member 38 may be unable to threadedly purchase with the near cortical wall 28. Instead, purchase between the bone fixation member 38 and the far cortical wall 30 can fix the bone fixation member 38, and thus the bone plate 34, to the underlying bone 26. As will be described in more detail below, the bone fixation member 38 can be a locking bone screw 39 having a head 43 that is threaded, or can be a compression screw 41 having a head 43 that is unthreaded (see FIG. 5B). Further, as will be described below, the fixation hole 40 can be a variable-angle locking hole 45 (see FIG. 4A) that is configured to threadedly mate with the threaded head 43 of the locking screw 39 that is oriented at any angle within a range of angles relative to the central axis of the bone fixation hole 40.

The bone plate 34 will now be described in more detail with reference to FIG. 2A. In particular, the bone plate 34 includes a bone plate body 42 that defines a bone facing surface 44 that is configured to face the underlying bone 26 during operation. The bone facing surface 44 is further configured to apply the compression force to the bone fragments 22 as described above. The bone plate body 42 also defines an outer surface 46 that is opposite the bone facing surface 44 along a transverse direction T. In particular, the bone facing surface 44 can be said to be opposite the outer surface 46 in an inward direction 47a. The outer surface 46 can be said to be opposite the bone facing surface 44 in an outward direction 47b that is opposite the inward direction 47a. Thus, the inward direction 47a and the outward direction 47b can be opposite directions that are both oriented along the transverse direction T. The bone plate can be made of any suitable biocompatible material, including but not limited to stainless steel, titanium, cobalt, chromoly, Nitinol, and alloys thereof.

The bone plate body 42 can define at least one hub 58 that circumferentially surrounds a respective one of the at least one bone fixation hole 40. Thus, when the bone plate 34 includes only a single bone fixation hole 40, the bone plate body 42 can similarly define only a single hub 58. In one example, the hub 58 can be cylindrical in shape and can extend from the outer surface 46 to the bone facing surface 44. It should be appreciated, of course, that the hub can define any suitable shape as desired. The hub 58 can define an interior surface 60 of the bone plate body 42 that defines the bone fixation hole 40. Thus, the interior surface 60 is configured to engage the bone fixation member 38 such that the bone fixation member 38 secures the bone plate 34 to the underlying bone 26. The interior surface 60 can extend from the outer surface 46 to the bone facing surface 44. The interior surface 60 can be oriented along the transverse direction T from the outer surface 46 to the bone facing surface 44. Alternatively, at least a portion of the interior surface 60 can taper radially inward toward the central axis of the bone fixation hole 40 as it extends from the outer surface 46 to the bone facing surface 44.

The bone plate body 42 can define a central location and an outer perimeter 50 that at least partially surrounds the central location. Further, the hub 58 can surround the central location. In one example, the central location can be defined by a geometric center of the bone plate body 42 such that a centerline oriented along the transverse direction T can pass through the geometric center. The outer perimeter 50 can be spaced radially outward with respect to the centerline and the bone fixation hole 40. Thus, the hub 58 can be disposed radially between the bone fixation hole 40 and the outer perimeter 50. In one example, the outer perimeter 50 can extend along a curved path that surrounds the centerline. The curved path can, in one example, be a circle. Thus, it can be said that the outer perimeter 50 can approximate a circle.

In this regard, because the bone plate 34 has a round shape in one example of the present disclosure, the bone plate 34 is described herein in terms of radial directions and circumferential directions. Thus, the bone plate 34 can be circular, oval, or any alternative round shape as desired. It should be appreciated, of course, that the bone plate 34 can define any suitable alternative shape as desired, such as square, triangular, or rectangular, among others. Thus, the radial direction as used herein can be replaced by a longitudinal direction L that is substantially perpendicular to the transverse direction T. Alternatively or additionally, the radial direction as used herein can be replaced by a lateral direction A that is substantially perpendicular to both the longitudinal direction L and the transverse direction T. It can further be said that the outer perimeter 50 extends circumferentially about the centerline along a circumferential direction. However, it should again be appreciated that the outer perimeter 50 can have any suitable size and shape as desired. Thus, the circumferential direction as used herein can be replaced by one or more directions that extend about an outer perimeter of the bone plate. The outer perimeter 50 can lie in a plane that is defined by the longitudinal direction L and the lateral direction A. Alternatively, portions of the outer perimeter 50 can be offset from each other along the transverse direction T.

In one example, the centerline can also define the central axis of the bone fixation hole 40. Thus, the bone fixation hole 40 can be disposed at the geometric center of the bone plate body 42, and the outer perimeter can at least partially surround the bone fixation hole 40. Alternatively, the central axis of the bone fixation hole 40 can be offset from the geometric center of the bone plate body 42 along a direction perpendicular to the transverse direction. Further, the central axis of the bone fixation hole 40 can be parallel with the centerline or can be angularly offset with respect to the centerline. In one example, the bone plate 34 includes only single bone fixation hole 40. Thus, the bone fixation hole 40 can be the only hole of the bone plate 34 that is configured to receive a permanent bone fixation member 38 that is inserted through the hole and into the underlying bone 26. Alternatively, the bone plate 34 can include a plurality of bone fixation holes 40 as desired that are each configured to receive a respective permanent bone fixation member that is inserted through the hole and into the underlying bone 26. The bone fixation holes 40 can be spaced about the centerline of the bone plate 34. For instance, the bone fixation holes 40 can be equidistantly spaced about the centerline.

A permanent bone fixation member is a bone fixation member that fastens the bone plate 34 to the underlying bone 26, and remains implanted after the surgical procedure has completed. Thus, the bone fixation member 38 can be referred to as a permanent bone fixation member. It is recognized that it might be decided to eventually remove the permanent bone fixation member 38 (along with the bone plate 34) after bone healing has occurred, or if a surgical revision procedure is to be performed. The single bone fixation hole 40 can be preferred in some instances as it allows for easier implantation of the bone plate 34 and can be sufficient to achieve fixation to the underlying bone 26.

Figure 2A:
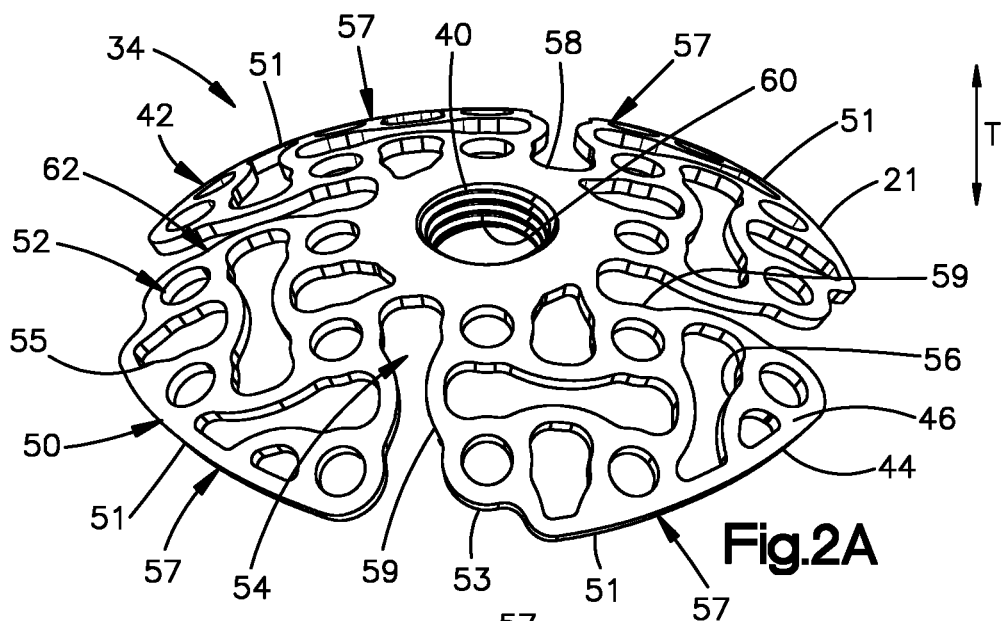
FIG. 2A is a perspective view of the bone plate illustrated in FIG. 1A.

Referring now to FIG. 2A, and as described above, the bone plate body 42, and thus the bone plate 34, can be flexible and resilient. For instance, in one example, the bone plate 34 can define at least one aperture 52, such as a plurality of apertures 52, that extend through the bone plate body 42 from the outer surface 46 to the bone facing surface 44. At least a select one of the apertures 52 can be open to the outer perimeter 50 of the bone plate body 42, and can thus be referred to as an outer aperture 54. The at least one outer aperture 54 of the apertures 52 can include a plurality of outer apertures 54. Each of the outer apertures 54 can extend radially through the outer perimeter 50. In one example, each of the outer apertures 54 can be configured as a slot that is elongate radially from the hub 58 through the outer perimeter 50. The outer apertures 54 can further be spaced circumferentially from each other. For instance, the outer apertures 54 can be equidistantly circumferentially spaced from each other. Alternatively, adjacent ones of the outer apertures 54 can be circumferentially spaced from each other at different distances.

Thus, the outer apertures 54 can divide the bone plate body 42 into a plurality of petals 57 that extend radially outward from the hub 58 to the outer perimeter 50. As will be appreciated from the description below, each of the petals 57 can be configured to apply a respective compressive force to the underlying bone fragments 22 when the bone plate 34 is moved from the loaded position 25 to the compression position 23. The petals 57 can each define a respective end walls 51 that each defines a respective portion of the outer perimeter 50. Thus, the end walls 51 can, in combination, define the outer perimeter 50. Further, the end walls 51 can define respective arcs that lie on a common circular path. In one example, the outer perimeter 50 can be continuous and uninterrupted at each of the petals 57. Each of the petals 57 can further be bounded circumferentially by a respective pair of side walls 59 that are circumferentially opposite each other. The side walls 59 can converge toward each other as they extend from the respective end wall 51 toward the hub 58. Further, the side walls 59 of each of the petals 57 can be oriented at least substantially parallel (e.g., within 15 degrees) or parallel with one of the side walls 59 of an adjacent one of the petals 57.

Thus, each of the petals 57 can define a respective outer petal perimeter 53 that is defined by a respective pair of the side walls 59 and the respective end walls 51. The side walls 59 can extend continuously and uninterrupted from the hub 58 of the outer perimeter 50. In one example, the side walls 59 can extend linearly from the hub 58 to the outer perimeter 50. Adjacent ones of the petals 57 can be separated from each other circumferentially by respective ones of outer apertures 54. Otherwise stated, the bone plate 34 defines the outer apertures 54 that separate the bone plate body 42 into the plurality of petals 57. Because the outer apertures 54 can be equidistantly spaced from each other, the outer petal perimeters 53 of each of the petals 57 can be substantially identical (e.g., within manufacturing tolerance) to each other. Alternatively, the outer apertures 54 can be variably spaced from each other. Accordingly, the outer petal perimeter 53 of at least one of the petals 57 can be greater than or less than the outer petal perimeter 53 of at least another one of the petals 57.

The apertures 52 of the bone plate 34 can further include a plurality of inner apertures 55 that extend through the bone plate body 42 along the transverse direction T from the outer surface 46 to the bone facing surface 44. At least some up to all of the inner apertures 55 can be fully enclosed about their respective perimeters by the bone plate body 42. In particular, at least some up to all of the inner apertures 55 can be fully enclosed about their respective perimeters by a respective one of the petals 57. Alternatively, at least one of the inner apertures 55 can extend through the outer petal perimeter 53. For instance, at least one of the inner apertures 55 can extend circumferentially through one or both of the end wall 51 and one the side walls 59. Thus it will be appreciated that the end wall 51 of at least one of the petals 57 can be interrupted by at least one of the inner apertures 55. Similarly, one or both of the side walls 59 can be interrupted by at least a respective one of the inner apertures 55.

The apertures 52 can combine so as to define interconnected linkages 56 of the bone plate body 42, and thus of the bone plate 34. The interconnected linkages 56 can be elastic and flexible. Further, the interconnected linkages 56 can be monolithic with each other. During operation, as the bone plate 34 moves in a direction from the first position to the loaded position, at least some of the linkages 56 elastically flex, thereby biasing the bone plate 34 to return from the loaded position toward the first position. The linkages 56 further bias the bone plate to return from the compression position to the first position.

Thus, it should be appreciated that the linkages 56 and apertures 52 can combine to define an elastically flexible region 62 that extends from the hub 58 to the outer perimeter 50. In one example, with continuing reference to FIG. 2A, the select ones 54 of the apertures 52 can extend from the outer perimeter 50 to the hub 58. Thus, it should be appreciated that the elastically flexible region 62 of the bone plate body 42 can extend from the hub 58 to the outer perimeter 50. Thus the hub 58 can be devoid of apertures 52 that extend through the bone plate body 42 from the outer surface 46 to the bone facing surface 44. Accordingly, one or both of the outer surface 46 and the bone facing surface 44 at the hub 58 can be continuous and uninterrupted from the bone fixation hole 40 to the flexible region 62. In one example, the flexible region 62 can be divided into the plurality of petals 57 by the outer apertures 54.

The bone plate 34 can include as many or as few apertures 54 as desired. In one example, the bone plate 34 can include as little as a single aperture 54 that allows the bone plate 34 to flex between the first position and the loaded position. Thus, the flexible region 62 can define only a single petal 57, and can be circumferentially continuous from a first one of the side walls 59 to an opposed second one of the side walls 59. The term circumferentially continuous in this context is intended to mean that there is no single aperture 52 that extends continuously from the hub 58 to the outer perimeter 50 at a location circumferentially between the first and second ones of the side walls 59. Alternatively, the bone plate 34 can include any number of apertures 52 as desired so as to define a corresponding number of petals 57 as desired. It can therefore be said that the bone plate body 42, and thus the bone plate 34, can include at least one petal 57. For instance, the bone plate body 42, and thus the bone plate 34, can include a plurality of petals 57. In one example, the bone plate body 42 includes four petals that are each disposed at a respective quadrant of the bone plate body 42.

The apertures 52 and linkages 56 can be configured such that each petal 57 can provide different levels of elasticity along its length from the hub 58 to its respective end wall 51. Thus, each petal can define a level of compression that varies along its length from the hub 58 to the respective end wall 51. In one example, the petals 57 define a level of elasticity that increases along a radially outward direction from the hub 58 to the respective end wall 51. Alternatively, the petals 57 can have a thickness that increases in the radially outward direction from the hub 58 that causes the level of elasticity to decrease along the radially outward direction. Accordingly, the petals 57 can apply a level of compression that increases or decreases along the radially outward direction from the hub 58 to the respective end wall 51. Alternatively, the apertures 52 and linkages 56 can be configured such that each petal 57 can provide a substantially constant (e.g., within manufacturing tolerance) level of elasticity along its length from the hub 58 to its respective end wall 51.

Alternatively or additionally, the apertures 52 and linkages 56 can be configured such that each petal 57 can provide different levels of elasticity along its width along a circumferential direction between the respective side walls 59. Alternatively, the apertures 52 and linkages 56 can be configured such that each petal 57 can provide a substantially constant (e.g., within manufacturing tolerance) level of elasticity along its width between the respective side walls 59.

Further, each petal 57 can have the same flexibility as all of the other petals 57. Thus, the apertures 52 and linkages 56 of each of the petals 57 can be at least substantially identical (within manufacturing tolerance) to the apertures 52 and the linkages 56 of all others of the petals 57. Otherwise stated, the petals 57 can be at least substantially symmetrical with each other. Accordingly, the bone plate 34 can be configured to provide substantially the same compression to the underlying bone fragments about an entirety of its outer perimeter 50 (see FIG. 1B). Alternatively, it should be appreciated that the bone plate 34 can be customized such that at least one of the petals 57 has greater flexibility than one or more of the other petals 57. For instance, the linkages 56 of one of the petals 57 can have different sizes and shapes with respect to the linkages 56 of at least one or more others of the petals 57. In this regard, a kit of customized bone plates 34 can be provided. Accordingly, certain ones of the petals 57 can be more flexible than the other petals 57. As a result, a first portion of the outer perimeter 50 can apply more compression to the underlying bone fragments 22 than a second portion of the outer perimeter 50. This can be useful, for instance, depending on the profile of the comminuted bone fracture 24 (see FIG. 1A). It will therefore be understood that the apertures 52 and linkages 56 of each of the petals 57 can be of any suitable size and shape as desired that provide for the desired compression against the underlying bone 26.

Figure 2B:
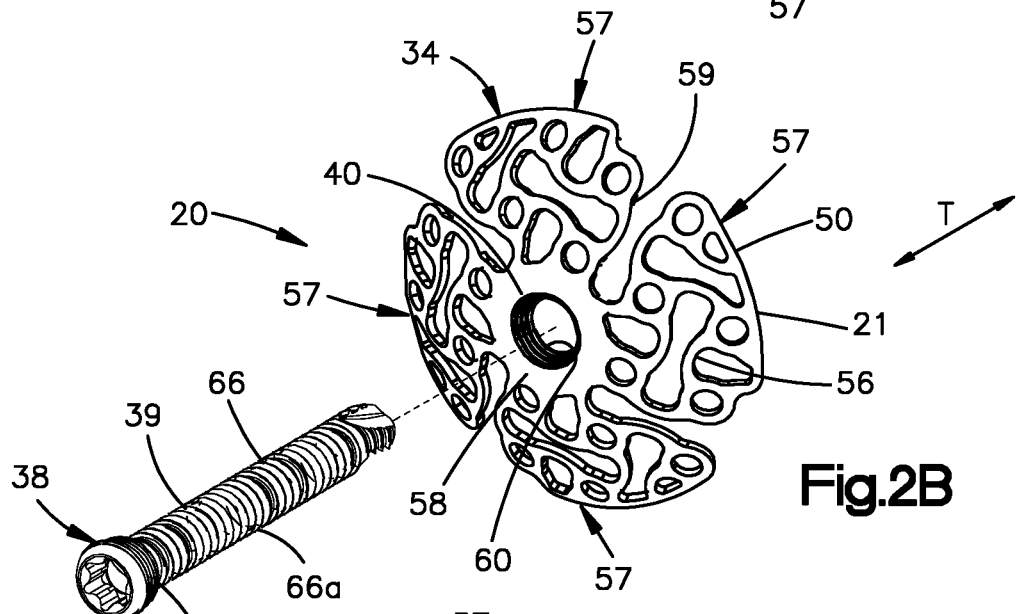
FIG. 2B is an exploded perspective view of the bone fixation system illustrated in FIG. 1A, showing the bone fixation member aligned to be inserted into a threaded bone fixation hole of the bone plate.
Figure 2C:
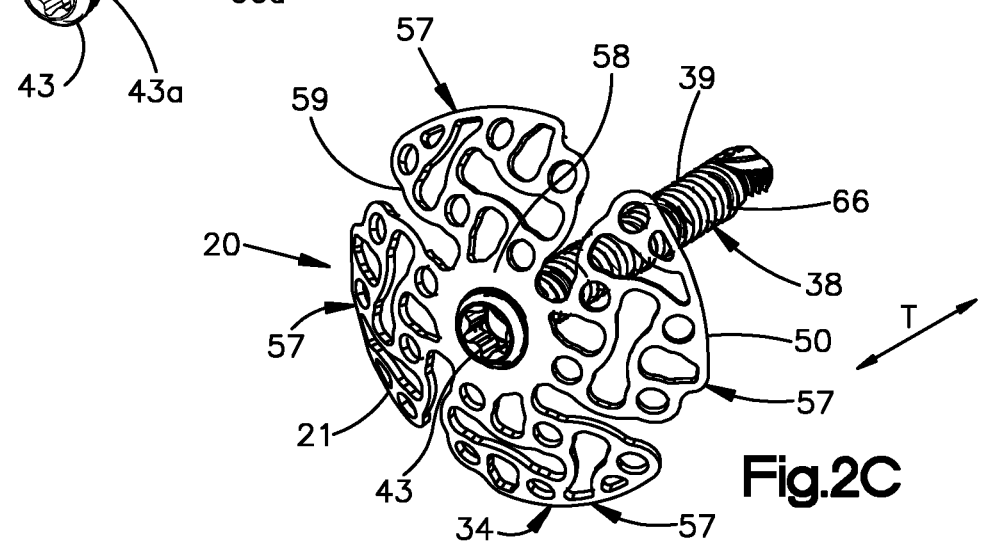
FIG. 2C is a perspective view of the bone fixation system illustrated in FIG. 1B, showing the bone fixation member attached to the bone plate in the bone fixation hole.

Referring now to FIGS. 2B-2C, as described above, the bone fixation member 38 can have a bone fixation head 43 and a bone fixation shaft 66 that extends out from the head 43 along a bone fixation axis. The head 43 is configured to engage the bone plate 34 in the bone fixation hole 40, such that the shaft 66 extends in the inward direction 47a into the underlying bone 26. The bone fixation shaft 66 defines an outer shaft surface 66a configured to engage the underlying bone 26. At least a portion of the outer shaft surface 66a can be threaded so as to threadedly purchase with the underlying bone 26. In particular, the outer shaft surface 66a at a distal free end of the shaft 66 can be threaded. The distal end of the shaft 66 can be spaced from the head 43 a sufficient distance so as to threadedly purchase with the far cortical wall 30 (see FIG. 3F) when the bone fixation member 38 is driven through the bone fixation hole 40. In one example, an entirety of the outer shaft surface 66a can be threaded. As described above, the head 43 can have an outer surface 43a that can likewise be threaded. Thus, the bone fixation member 38 can be configured as a locking screw 39. The interior surface 60 of the bone plate body 42 can be threaded so as to threadedly purchase with the threaded outer surface 43a of the head 43.

Referring now to FIG. 3A, the bone plate 34 is configured to receive a biasing force that causes the bone plate 34 to move from the first position 21 to the loaded position 23. In one example, the bone fixation system 20 can include an insertion instrument 70 that is configured to grip the bone plate 34 when the bone plate 34 is in the loaded position 23. The insertion instrument 70 can further be configured to guide the bone fixation member 38 into the bone fixation hole 40. In particular, the insertion instrument 70 can include a cannula 71 that is configured to receive the bone fixation member 38 and direct the bone fixation member toward the bone fixation hole 40.

The insertion instrument 70 can include a gripper 72 that is configured to engage the bone plate body 42, and thus the bone plate 34, when the bone plate 34 is in the loaded position 21. The gripper 72 can be configured to apply a counterforce to the bone plate 34 in the outward direction 47b when the bone plate 34 receives a biasing force in the inward direction 47a that retains the bone plate 34 in the loaded position, even as the bone plate 34 is intrinsically urged to move from the loaded position toward the first position 21. The biasing force can be applied by the cannula 71. In another example, the gripper can grip the bone plate 34 in the first position 21, and the cannula 71 can bias the bone plate 34 from the first position to the loaded position 23. The counterforce can then further maintain the bone plate 34 in the loaded position. In one example, the gripper 72 can grip the bone plate 34 at the outer perimeter 50. It should be appreciated, of course, that the gripper 72 can grip the bone plate 34 at any location on the bone plate body 42 as desired. The gripper 72 can include a gripper body 79 and a plurality of gripper arms 75 that extend radially out from the gripper body 79. The gripper 72 can include a central opening 81 that extends through the gripper body 79 along the transverse direction T so as to receive the cannula 71 as described in more detail below. The gripper arms 75 can be circumferentially spaced from each other and each configured to grip the bone plate body 42, and thus the bone plate 34. The gripper arms 75 can be movable radially inward so as to grip the bone plate body 42, and movable radially outward so as to disengage the bone plate body 42. For instance, the gripper arms 75 can be barbed, and can be flexible and resilient such that the barbs cam over and engage the bone plate 34 with enough force such that the gripper arms 75 can provide the counterforce without disengaging from the bone plate 34.

it should thus be appreciated that the insertion instrument 70 can include a biasing member 74 that is configured to apply an inward force to the bone plate 34. The biasing member 74 can be defined by the cannula 71. Alternatively, the biasing member 74 can be defined by any alternative structure suitable to apply the inward force to the bone plate 34. The inward force can maintain the bone plate 34 in the loaded position 23. Additionally, the inward force can bias the bone plate 34 from the first position 21 to the loaded position 23. Thus, the inward force can also be referred to as a biasing force. In particular, the biasing member 74 can define an engagement surface 76 that is configured to abut the outer surface 46 and apply the biasing force to the outer surface 46 in the inward direction 47a. The engagement surface 76 can be disposed at a distal end of the biasing member 74. It may be desirable for the gripper 72 to grip the bone plate 34 at a location disposed radially outward from the location where the insertion instrument 70 applies the inward force to the bone plate 34.

The gripper 72 can be movable with respect to the biasing member 74 along the transverse direction T. For instance, referring to FIG. 3B, the biasing member 74 can be moved in the inward direction 47a with respect to the gripper 72 so as to retain the bone plate 34 from in the loaded position 23. Thus, the bone plate 34 can be moved from the first position 21 to the loaded position 23 prior to engagement with the insertion instrument 70. In one example, the bone plate 34 can be responsive to temperature fluctuations that can maintain the bone plate 34 in the loaded position 23, and can further cause the bone plate 34 to move from the loaded position 23 to the compression position 25. In particular, the bone plate 34 can be made from a shape memory material that can maintain the bone plate 34 in the loaded position 23. Further, the shape memory material can be a temperature-sensitive material In one example, the bone plate 34 can be made of Nitinol. Any suitable auxiliary structure can be used to move the bone plate 34 from the first position 21 to the loaded position 23. Alternatively, the bone plate 34 can be substantially flattened manually from the first position 21 to the loaded position 23.

Thus, the bone plate 34 at a warm temperature can be moved from the first position to the loaded position 23. In particular, the bone plate 34 can be substantially flattened. The warm temperature can, for instance, be room temperature. Next, once the bone plate 34 is moved to the loaded position 23 in any suitable manner as desired, the bone plate 34 can be subjected to cold temperatures while the bone plate 34 is in the loaded position 23 so as to cool the bone plate 34 to a cooled temperature that causes the bone plate 34 to lose its elasticity. Thus, when the temperature of the bone plate 34 is lowered to the cooled temperature while in the loaded position 23, the bone plate 34 is maintained in the loaded position 23. The temperature of the bone plate 34 can be lowered to the cooled temperature at a location remote from the bone 26. In one example, the coolant can be liquid nitrogen. It should be appreciated, however, that any suitable alternative coolant can be used. Once the bone plate is at a cooled temperature, the bone plate 34 loses its elasticity and is therefore naturally maintained in the loaded position 23.

When the bone plate 34 is subsequently subjected to heat, the temperature of the bone plate 34 increases to the heated temperature that causes the bone plate 34 to regain its elasticity. Thus, when the bone plate 34 is heated to the heated temperature, the bone plate body 42 can naturally bias the bone plate 34 from the loaded position 21 toward the first position 23. As a result, when the bone plate 34 is placed against the underlying bone 26 and warmed to the heated temperature, the bone plate can move from the loaded position 23 to the compression position 25 in the manner described above. In one example, the anatomical body temperature of the patient can cause the temperature of the bone plate 34 to rise to the heated temperature. Accordingly, the bone plate 34 can be placed against the underlying bone 26, such that the temperature of the anatomical environment surrounding the bone 26 can raise the temperature of the bone plate 34 to the heated temperature. Thus, the bone plate body 42 can naturally bias the bone plate 34 to the compression position 25 described above. Alternatively or additionally, an external heat source can cause the temperature of the bone plate 34 to rise to the heated temperature. Thus, as illustrated in FIG. 3B, the gripper 72 can grip the bone plate 34 and the biasing member 74 can engage the bone plate 34 after the bone plate 21 has been moved from the first position 21 to the loaded position 23. It should be appreciated that when the bone plate 34 is made from a temperature-sensitive shape memory material, the bone plate 34 can be placed against the underlying bone in the loaded position without the aid of an insertion instrument. Alternatively, the insertion instrument 70 can be used to implant the bone plate 34 in any manner described herein.

Figure 3C:
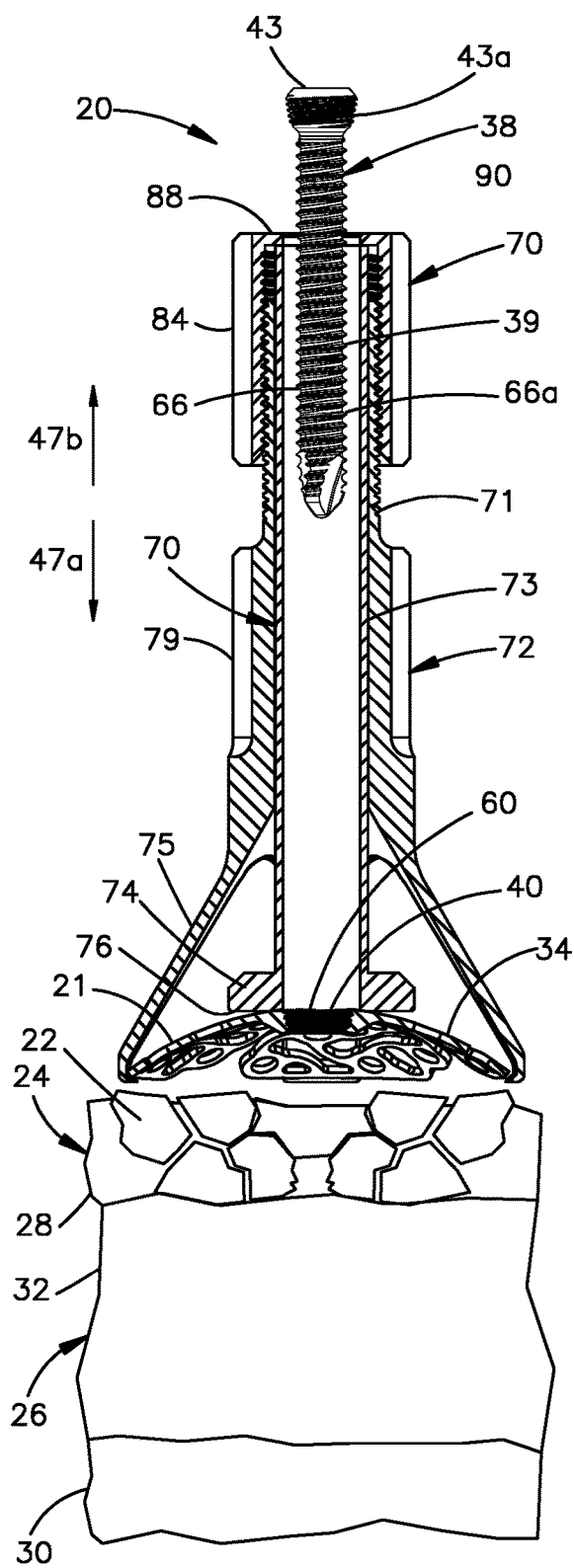
FIG. 3C is a sectional side elevation view of the bone fixation system illustrated in FIG. 3A, showing the insertion instrument coupled to the bone plate while the bone plate is in the first position.
Figure 3D:
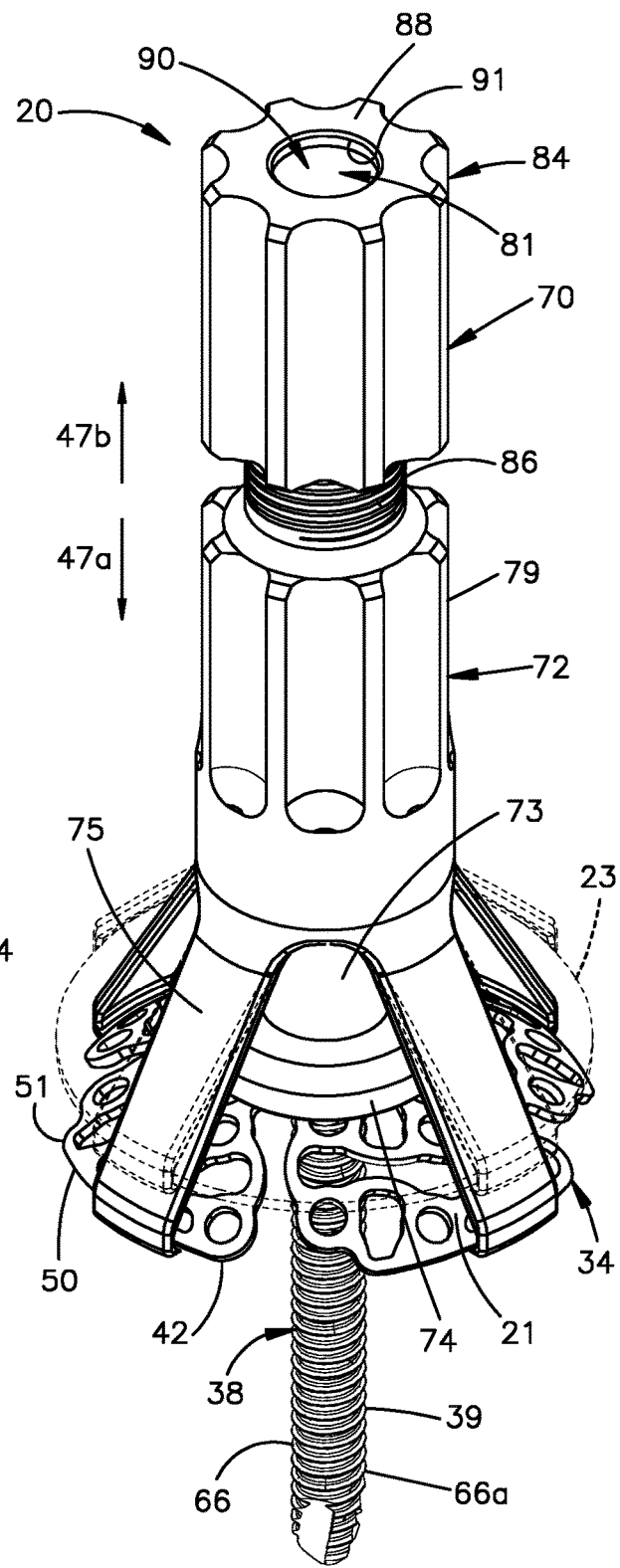
FIG. 3D is a perspective view of the bone fixation system illustrated in FIG. 3C, showing the insertion instrument coupled to the bone plate, and further showing iteration of the insertion instrument causing the bone plate to move from a first position to a loaded position.

Alternatively, referring to FIGS. 3C-3D, the biasing member 74 can be moved in the inward direction 47a with respect to the gripper 72 so as to move the bone plate 34 from the first position 21 to the loaded position 23. Thus, the gripper 72 can grip the bone plate 34 when the bone plate 34 is in the first position 21. Next, the biasing member 74 can be moved in the inward direction 47a with respect to the gripper 72 as the engagement surface 76 is in contact with the bone plate 34 at the outer surface 46, such that the engagement surface 76 applies the biasing force to the outer surface 46 that causes the bone plate 34 to move from the first position 21 to the loaded position 23. It should be appreciated that the insertion instrument 70 can be configured to move the bone plate 34 from the first position 21 to the loaded position 23 before the bone plate 34 has been placed against the underlying bone, or after the bone plate 34 has been placed against the underlying bone.

The bone plate 34 can further be chilled in the manner described above as the biasing member 74 applies the biasing force to the bone plate 34. It can further be said that the gripper 72 can be moved in the outward direction 47b with respect to the biasing member 74 as the engagement surface 76 is in contact with the bone plate 34 so as to move the bone plate 34 from the first position 21 to the loaded position 23. Whether the gripper 72 is moved in the outward direction 47b with respect to the biasing member 74, or the biasing member 74 moves in the inward direction 47a with respect to the gripper 72, the biasing member 74 can be said to provide the biasing force while the gripper 72 provides the counterforce. Whether the bone plate 34 is moved from the first position 21 to the loaded position 23 before or after the instrument 70 engages the bone plate 34, it can be said that the instrument 70 provides a biasing force that maintains the bone plate 34 in the loaded position 23. When the bone plate 34 is moved from the first position 21 to the loaded position 23, the curvature of the bone plate 34 can be reduced. Thus, the natural curvature of the bone plate 34 can cause the bone plate 34 to be naturally biased toward the first position from the loaded position. In one example, the bone facing surface 44 can be substantially planar when the bone plate 34 is in the loaded position 23, as illustrated in FIG. 3E.

Referring again to FIG. 3A, the biasing member 74 can be defined by the cannula 71. In particular, the cannula 71 can include a cannulated wall 73, and the biasing member 74 can extend radially outward from a distal end of the cannulated wall 73. The cannulated wall 73 can be radially sized to fit inside the opening 81 of the gripper body 79. The biasing member 74 can be radially sized greater than the opening 81. The biasing member 74 can define a distal end that defines the engagement surface 76. Thus, the engagement surface 76 can apply the biasing force to the insertion instrument 70 at a location adjacent the bone fixation hole 40. The cannulation of the cannula 71 can be aligned with the bone fixation hole 40 along the transverse direction when the gripper arms 75 grip the bone plate 34. The engagement surface 76 can be configured to at least partially surround an opening to the bone fixation hole 40. The opening can be defined at the outer surface 46.

The insertion instrument 70 can further include a coupler 84 that is configured to engage the cannula 71 and the gripper 72 so as to maintain the biasing force against the bone plate 34. In particular, the gripper body 79 can have a proximal end 86 that is configured to attach to the coupler 84. In one example, the proximal end 86 can be threaded, and the coupler 84 can be threaded and configured to threadedly mate with the proximal end 86 of the gripper body 79. Thus, the coupler 84 can be threadedly attached to the gripper body 79, thereby securing the coupler 84 to the gripper 72. In one example, the coupler 84 can be configured as a knob. The coupler 84 can include a stop wall 88 that covers at least a portion of the opening 81 when the coupler 84 is secured to the gripper 72. Thus, at least a portion of the stop wall 88 is aligned with at least a portion of the cannulated wall 73 when the cannulated wall 73 is inserted in the opening 81 and the coupler 84 is secured to the gripper 72. As a result, the cannula 71 can be captured between the bone plate 34 that is engaged by the gripper arms 75 and the stop wall 88. It should be appreciated that as the coupler 84 is advanced along the inward direction 47a toward the bone plate 34, the distance between the stop wall 88 and the bone plate 34 is reduced until the coupler 84 is in a fully seated position on the gripper 72.

It can be said that the coupler 84 is fully seated when interference between the coupler 84 and the gripper 72 prevents the coupler 84 from advancing toward the bone plate 34 in the inward direction 47a. For instance, in one example the coupler 84 is fully seated on the gripper 72 when the stop wall 88 contacts the proximal-most surface of the proximal end 86 of the gripper 72. It should be appreciated, of course, that the coupler 84 at any suitable location can interfere with the gripper 72 at any suitable alternative location when the coupler 84 is fully seated on the gripper 72. Alternatively still or additionally, the coupler 84 can be said to be fully seated on the gripper 72 when the coupler 84 prevents the cannula 71 from moving away from the bone plate 34 a sufficient distance so as to allow the bone plate 34 to move from the loaded position 23 toward the first position 21. In one example, the cannula 71 can be sized along the transverse direction T such that when the coupler 84 is fully seated on the gripper 72, the biasing member 74 maintains the bone plate 34 in the loaded position 23, as illustrated in FIG. 3E. When the gripper arms 75 grip the bone plate 34, interference between the cannula 71 and the stop wall 88 causes the biasing member 74 to maintain contact with the outer surface 46 of the bone plate 34, thereby preventing the bone plate 34 from deforming from the loaded position 23 toward the first position 21.

During operation, the cannulated wall 73 is inserted into the opening 81 of the gripper 72 along the outward direction 47b. The gripper arms 75 can then be removably attached to the bone plate 34 in the manner described above. Finally, the coupler 84 can be move to a fully seated position on the gripper 72 in the manner described above. In some examples, the coupler 84 can be secured to the gripper 72 prior to the step of inserting the cannulated wall 73 into the opening 81. Alternatively, the coupler 84 can be secured to the gripper after the step of inserting the cannulated wall 73 into the opening 81, but before the step of removably attaching the gripper arms 75 to the bone plate 34. Alternatively still, the coupler 84 can be secured to the gripper after the step of inserting the cannulated wall 73 into the opening 81, and after the step of removably attaching the gripper arms 75 to the bone plate 34. If desired, the coupler 84 can be fully seated on the gripper 72 before one or both of the steps of inserting the cannulated wall 73 into the opening 81, and removably attaching the gripper arms 75 to the bone plate 34.

Referring to FIG. 3D, the insertion instrument 70 can alternatively used to iterate the bone plate 34 from the first position 21 to the loaded position 23 as described above. Thus, during operation, the cannulated wall 73 can be inserted into the opening 81, and the gripper arms 75 can be removably attached to the bone plate 34 in the manner described above. Because the bone plate 34 is in the first position, the cannulated wall 73 will abut the stop wall 88 of the coupler 84. As the coupler 84 is subsequently fully seated on the gripper 72, the coupler 84 moves in the inward direction 47a with respect to the bone plate 34. Thus, the stop wall 84 similarly causes the cannula 71 to move in the inward direction 47a with respect to the bone plate 34, thereby causing the bone plate 34 to move from the first position 21 to the loaded position 23.

Referring now also to FIGS. 3E-3F, the insertion instrument 70 can be manipulated so as to place the bone plate 34 against the underlying bone 26 while in the loaded position 23. In particular, the bone plate 34 can be placed against the underlying bone 26, such that at least a portion of at least some of the fragments 22 are disposed inside the outer perimeter 50 of the bone plate 34 with respect to the radial direction. It can thus be said that at least a portion of at least some of the fragments 22 are disposed within a footprint of the bone plate 34 that is defined by the outer perimeter 50. For instance, an entirety of the bone fragments 22 that are to be compressed against each other by the bone plate 34 can be disposed inside the outer perimeter 50 of the bone plate 34 with respect to the radial direction.

Next, the bone fixation member 38 can be inserted through the bone fixation hole 40 and into the underlying bone. In particular, the coupler 84 can include an aperture 90. that extends through the stop wall 88. The aperture 90 can be defined by a threaded inner surface 91 of the coupler 84 that is configured to threadedly mate with the gripper 72 as described in more detail below. The aperture 90 can further extend entirely through the coupler 84. The aperture 90 can be aligned with the cannulation of cannula 71 and the bone fixation hole 40 along the transverse direction T. Accordingly, the bone fixation member 38 can be inserted through the aperture 90 of the coupler 84 and through the cannula 71. The cannula 71 can guide the bone fixation member 38 to the bone fixation hole 40. The bone fixation member 38 can be driven through the bone fixation hole 40 and into the underlying bone 26 until the head 43 is inserted into the bone fixation hole 40.

When the bone fixation member 38 is configured as the locking screw 39, the bone fixation member can be rotatably driven into the underlying bone 26 until the threaded outer surface 43a of the head 43 threadedly purchases with the threaded interior surface 60 of the bone plate 34. The bone fixation member 38 can be self-tapping as desired. Alternatively, a pilot hole can be drilled into the underlying bone 26, and the shaft 66 can be driven into the pilot hole so as to purchase with the underlying bone 26. When the thread pitch at the shaft 66 is equal to the thread pitch at the head 43, driving the bone fixation member 38 into the underlying bone 26 will not compress the bone plate 34 against the underlying bone 26. Alternatively, the thread pitch at the shaft 66 can be greater than the thread pitch at the head 43, such that the bone fixation member 38 will cause the compress the bone plate 34 to compress against the underlying bone 26 as it is driven into the bone 26 and purchases with the bone plate 34.

As the bone fixation member 38 is driven through the bone 26, the shaft 66 is driven through the near cortical wall 28 and the cancellous bone portion 32, until the threaded outer shaft surface 66a threadedly purchases with the far cortical wall 30. In particular, the threaded outer shaft surface 66a can threadedly purchase with the far cortical wall 30 as the head 43 is inserted into the bone fixation hole 40 of the bone plate 34. When the bone fixation member 38 is configured as the locking bone screw 39, the threaded outer shaft surface 66a can threadedly purchase with the far cortical wall 30 as the head 43 is (see FIG. 3F) as the threaded outer surface 43a of the head 43 threadedly purchases with the threaded interior surface 60 of the bone fixation hole 40. Thus, the bone fixation member 38 can fasten the bone plate to the underlying bone 26 as the bone facing surface 44 faces the underlying bone 26. In particular, the bone facing surface 44 can abut at least some of the bone fragments 22. For instance, the bone facing surface 44 can abut those bone fragments that are inside the footprint of the bone plate 34 and define an outer surface of the bone 26.

Next, the insertion instrument 70 can be disengaged from the bone plate 34, such that the bone plate 34 can be allowed to iterate to the compression position 25 from the loaded position 23. In particular, the gripper arms 75 can be removed from the bone plate 34 so as to detach the insertion instrument 70 from the bone plate 34. If the tension applied to the bone plate 34 from the cannula 71 is too great to remove the gripper arms 75 from the bone plate 34, then the coupler 84 can be removed from the fully seated position by moving the coupler 84 away from the bone plate 34. For instance, the coupler 84 can be moved along the gripper 72 in the outward direction 47b from the fully seated position to an unseated position. When the coupler 84 is in the unseated position, a distance between the stop wall 88 and the bone plate 34 is greater than the length of the cannula 71, such that insertion instrument 70 no longer prevents the bone plate 34 from moving from the loaded position 23 toward the first position 21. In particular, the insertion instrument 70 no longer prevents the bone plate 34 from moving from the loaded position 23 to the compression position 25. As described above, the coupler 84 can be threadedly advanced along the gripper 72 between the fully seated position and the unseated position. If the gripper arms 75 are unable to be disengaged from the bone plate 75 when the coupler 84 is in the fully seated position, the gripper arms 75 can be disengaged from the bone plate 75 after the coupler has moved from the fully seated position to the unseated position. In one example, the coupler 84 can be fully removed from the gripper 72.

As illustrated in FIG. 3F, once the insertion instrument 70 has been disengaged from the bone plate 34, the bone plate 34 can move from the loaded position 23 to the compression position 25. In particular, the temperature of the ambient environment can raise the temperature of the bone plate 34 from the cooled temperature that was used to iterate the bone plate 34 to the loaded position. Thus the bone plate 34 can regain its elasticity and move from the loaded position 23 to the compression position 23.

As will now be described, the bone plate 34 applies a compressive force to the bone fragments 22 when in the compression position 25. In one example, the insertion instrument 70 can be removed from the bone plate 34, which removes both the biasing force and the counterforce that maintained the bone plate 34 in the loaded position 23. As described above, the bone plate 34 can be naturally biased to move from the loaded position 23 toward the first position 21. Assuming no plastic deformation of the bone plate body 42 occurs when it moves to the loaded position 23, the bone plate 34 can be biased to return to the first position 21, which can be the natural position of the bone plate 34. If some plastic deformation occurs when the bone plate 34 moves to the loaded position 23, the bone plate can be biased to return to a natural position that is between the first position 21 and the loaded position 23. Either way, the compression position 25 is between the loaded position 23 and the first position 21.

However, the bone fragments 22 can prevent that bone plate 34 from moving all the way to the natural position. Accordingly, the bone plate 34 applies a compressive force to the bone fragments 22 when it is in the compression position 25 that is between the loaded position 23 and the first position. In particular, at least a portion of the bone plate body 42 can be offset in the inward direction 47a that is oriented along the transverse direction T when the bone plate 34 is in the compression position 25 with respect to when the bone plate 34 is in the loaded position 23. For instance the outer perimeter 50 of the bone plate can be biased in the inward direction 47a with respect to the central location of the bone plate body 42 as the bone plate 34 iterates from the loaded position 23 to the compression position 25. Thus, when the bone plate 34 is in the compression position, the outer perimeter 50 is offset in the inward direction 47a with respect to when the bone plate 34 is in the loaded position 23. In one example, the bone plate body 42 can resiliently bias the petals 57 in the inward direction 47a relative to the central location when the bone plate 34 iterates from the loaded position 23 to the compression position 25. Thus, each of the end walls 51 of the petals can apply the compression force to the underlying bone fragments in the inward direction 47a. Thus, the bone plate 34 can compress the bone fragments 22 against each other along the transverse direction T when the bone plate 34 moves from the loaded position 23 to the compression position 25.

Alternatively or additionally, the bone plate 34 can cause the bone fragments 22 to compress against each other along the radial direction. In particular, the bone facing surface 44 of the bone plate 34 can be concave when in the first position 21, less concave in the compression position 25 than when in the first position 21, and still less concave when the bone plate 34 is in the loaded position 23. Thus, moving the bone plate 34 to the compression position can increase the curvature of the bone plate 34. The bone plate 34 can apply a radial compressive force to the bone fragments 22 when the bone facing surface 44 is less concave than when the bone plate 34 is in the first position 21. In particular, the bone plate body 42 can resiliently bias the bone facing surface 44 to increase its concavity, which causes the outer perimeter 50 to apply a radially inwardly directed compression force to the bone fragments. For instance, the end walls 51 can be naturally biased in the radially inward direction when the bone plate 34 is in the compression position. Thus, it will be appreciated that the bone plate 34 can be configured to apply compressive forces to the underlying bone fragments 22 in both the inward direction 47a and the radially inward direction. The compressive forces applied by the bone plate 34 to the bone fragments 22 can reduce or remove the gaps between the bone fragments 22 such that the bone fragments 22 contact each other, thereby improving bone healing.

When the bone fixation member 38 configured as a locking screw 39, it can be threadedly mated with the threaded interior surface 60 when it is oriented such that the bone fixation axis of the bone fixation member 38 is aligned with the central axis of the bone fixation hole 40 as described above. Alternatively, referring to FIGS. 4A-4C, the bone fixation hole 40 can be configured as the variable-angle locking hole 45.

For instance, the interior surface 60 of the bone plate body 42 can define threads 82, and the bone plate body 42 can include a plurality of scalloped portions 77 that extend into the interior surface 60 and interrupt the threads 82. The bone plate body 42 can include any number of scalloped portions 77 as desired, such as four. The scalloped portions 77 separate the threads 82 into a corresponding plurality of columns 78 that are circumferentially spaced from each other. Accordingly, the scalloped portions 77 are disposed between adjacent ones of the columns 78 along the circumferential direction about the central axis of the bone fixation hole 40. The scalloped portions 77 can extend from the outer surface 46 to the bone facing surface 44. The scalloped portions 77 can be, for example, substantially cylindrically shaped as they extend circumferentially. Because the scalloped portions 77 extend radially outward beyond the interior surface 60, the scalloped portions 77 provide clearance that can extend the range of angulation of the bone fixation member 38 when the bone fixation member 38 is inserted into the bore fixation hole 40. In particular, the scalloped portions 77 are sized to receive at least a portion of the bone fixation shaft 66. Each of the scalloped portions 77, the columns 78, as well as the bone fixation member 38, can be configured substantially as described in U.S. Patent Application Publication No. 2010/0312286 and U.S. Pat. No. 9,149,316, the disclosures of each of which are hereby incorporated by reference in their entireties as if set forth herein.

In accordance with the illustrated embodiment, the bone fixation hole 40 can be defined by a plurality of columns 78 that are circumferentially spaced from each other about the interior surface 60. Adjacent ones of the columns 78 are separated from each other by respective ones of the scalloped portions 77. For instance, the columns 78 can be substantially equidistantly spaced from one another. Thus, the scalloped portions 77 can define respective widths, measured circumferentially, that are substantially equal to one another. While four columns 78 are illustrated, it should be appreciated, however, that the bone fixation hole 40 can include any number of columns 78 arranged in any number of patterns as desired. Furthermore, it should be appreciated that the columns 78 can alternatively be spaced about the interior surface 60 by varying distances, and the columns 78 and scalloped portions 77 can have different circumferential widths as well.

The scalloped portions 77 can divide the threads 82 into thread segments 80 that are adapted and configured to engage the threaded outer surface 43a of the head 43 of the bone fixation member 38, which is configured as the locking screw 39. The thread segments 80 can extend, for example, along paths which, if continued across respective gaps defined by the scalloped portions 77, would form a helical threading with a substantially constant pitch corresponding to the threaded outer surface 43a of the head 43 of the bone anchor described above with respect to FIGS. 2A-3F.

Accordingly, the bone plate body 42, and thus the bone plate 34, is configured to threadedly mate with the threaded outer surface 43a of the bone fixation head 43 when the central axis 61 of the shaft 66 is oriented at any angle within a range of angles relative to the central axis of the bone fixation hole 40. The range of angles can range from 0 degrees. to 45 degrees relative to the central axis 49 of the bone fixation hole 40. At 0 degrees, the shaft 66 is oriented coaxially with the central axis of the bone fixation hole 40. In an alternative embodiment, the range of angulation is can be from 0 degrees to approximately 15 degrees relative to the central axis of the bone fixation hole 40. It should be appreciated, of course, that the range of angles can vary as desired. Accordingly, the bone fixation member 38 can be angled with respect to the central axis of the bone fixation hole 40 such that the shaft threadedly purchases with the far cortical wall 30 at a desired location among a plurality of potential locations.

Figure 5A:
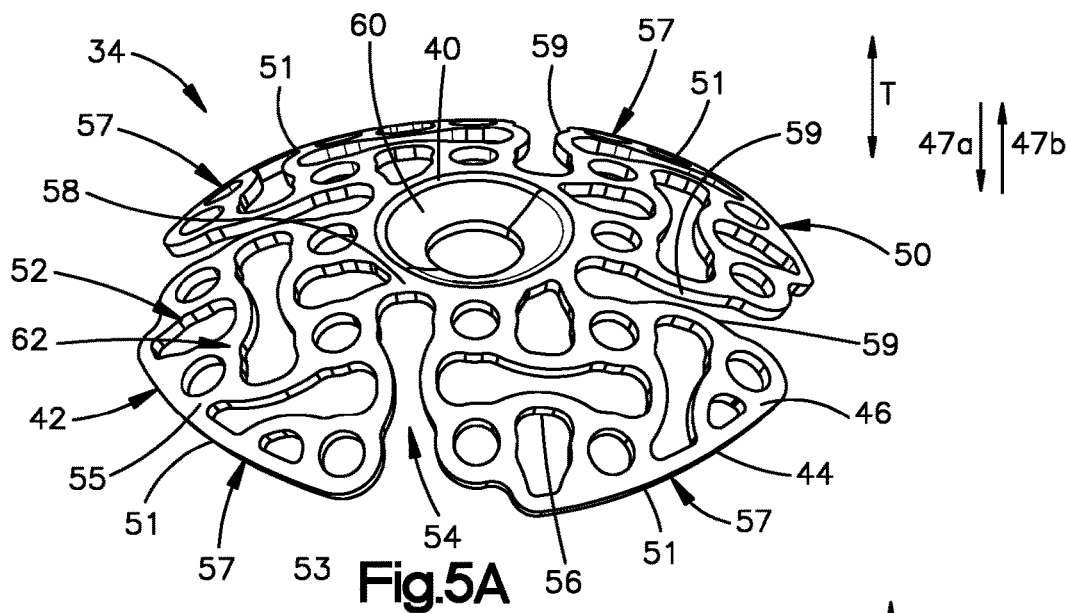
FIG. 5A is a perspective view of the bone plate similar to FIG. 2A, but including an unthreaded compression bone fixation hole in accordance with another embodiment.
Figure 5C:
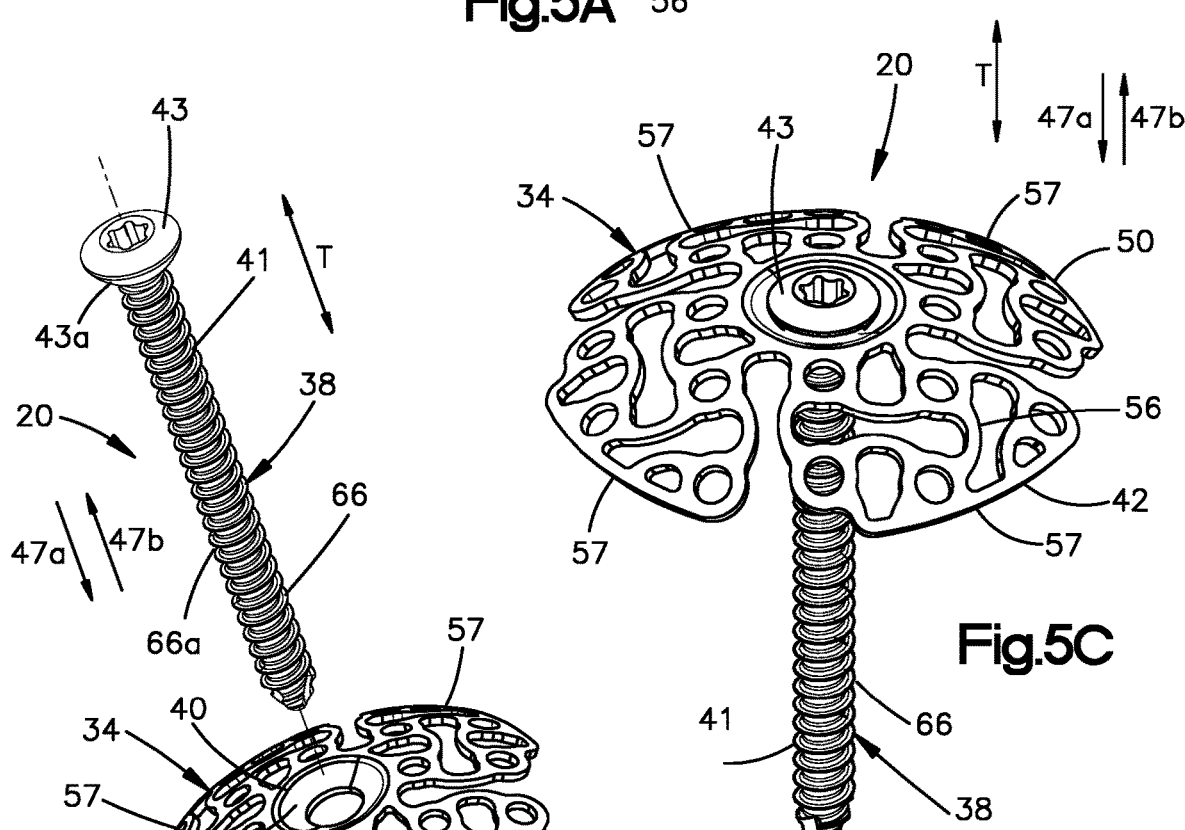
FIG. 5C is a perspective view of the bone fixation system illustrated in FIG. 5B, showing the bone fixation member inserted into the bone fixation hole.
Figure 5B:
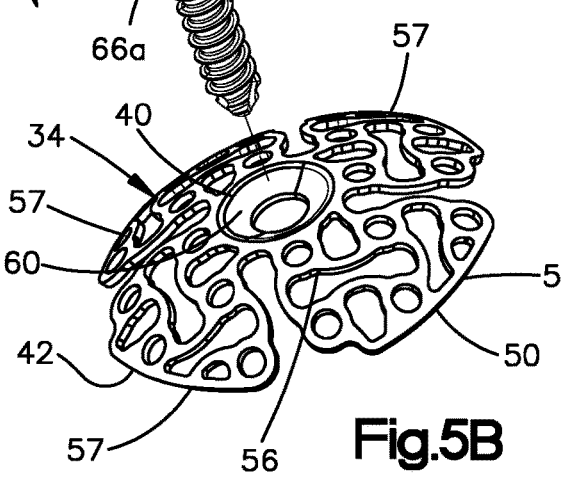
FIG. 5B is an exploded perspective view of the bone fixation system illustrated in FIG. 5A, showing the bone fixation member aligned to be inserted into the bone fixation hole of the bone plate.
Figure 7A:
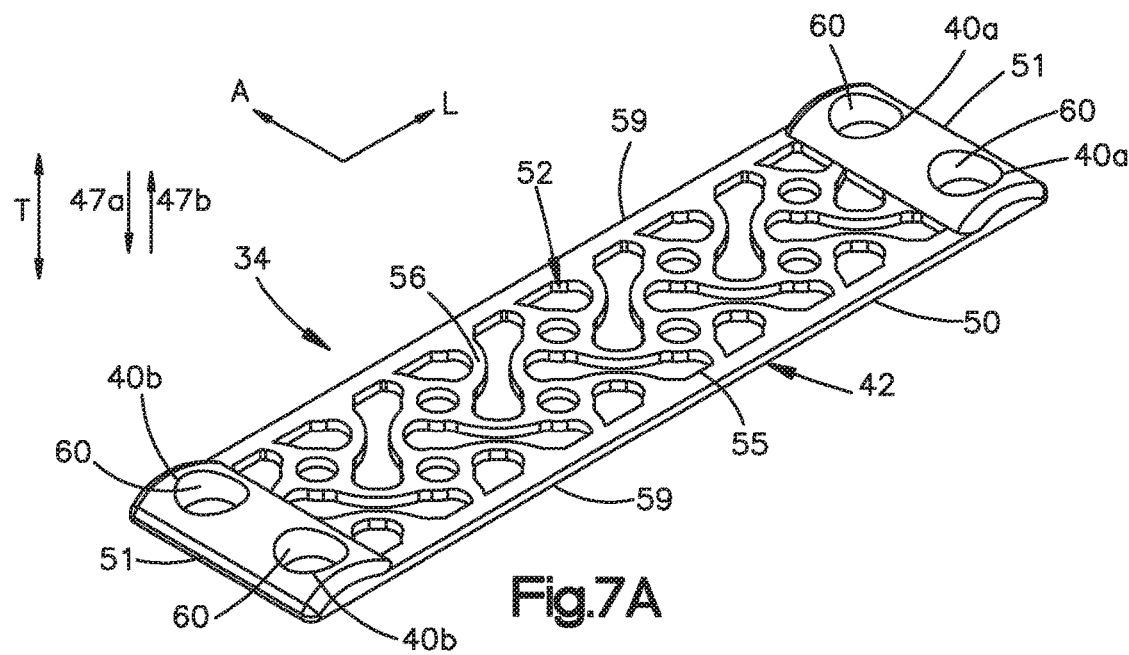
FIG. 7A is a perspective view of a bone plate constructed in accordance with an alternative embodiment.
Figure 7B:
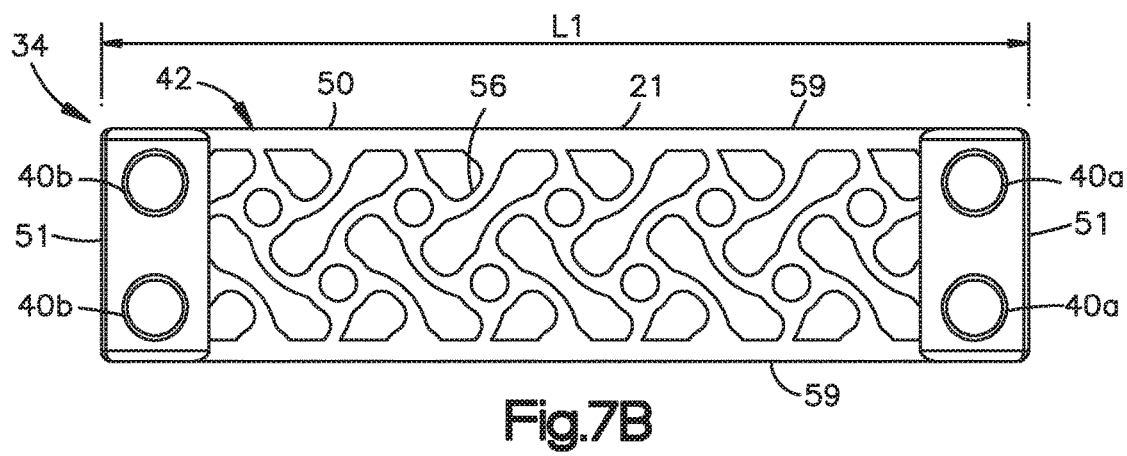
FIG. 7B is a top plan view of the bone plate illustrated in FIG. 7A shown in a first position having a first length.
Figure 7C:
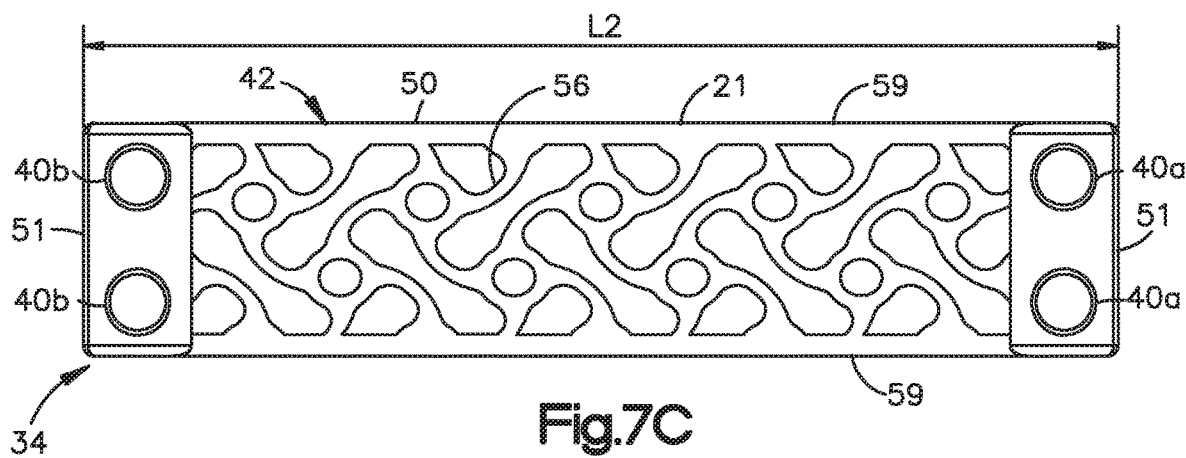
FIG. 7C is a top plan view of the bone plate illustrated in FIG. 7B, shown expanded to a loaded position having a second length that is greater than the first length.

Referring now to FIGS. 5A-5C, and as described above, the bone fixation member 38 be configured as a compression screw 41 that is configured to compress the bone plate 34 against the underlying bone 26. Thus, the outer surface 43a of the head 43 of the bone fixation member 38 can be unthreaded. Alternatively or additionally, the interior surface 60 of the bone plate body 42 can similarly be unthreaded. Accordingly, when the head 43 of the bone fixation member 38 bears against the interior surface 60, the head 43 can apply a compression force to the bone plate 34 that urges the bone plate 34 to move in the inward direction 47a. When the bone plate 34 is placed against the underlying bone 26, the compression force compresses the bone plate 34 against the underlying bone 26. Because the compression screw 41 does not threadedly mate with the bone plate 34 in the bone fixation hole 40, the shaft 66 can be oriented at any angle relative to the central axis of the bone fixation hole 40 as desired. Thus, the shaft 66 can threadedly purchase with the far cortical wall 30 at a desired location among a plurality of potential locations.

Referring now to FIGS. 6A-6C, and as described above, the bone plate 34 is configured to receive a biasing force that causes the bone plate 34 to move from the first position 21 to the loaded position 23. The biasing force can be applied by the insertion instrument 70 in the manner described above. Accordingly, once the bone plate 34 is in the loaded position 23 the compression screw 41 can be driven through the bone fixation hole 40 and into the underlying bone 26. The compression screw 41 can be driven through the bone fixation hole 40 before or after the bone plate 34 has been placed against the underlying bone 26. The compressive forces that the compression screw 41 applies to the bone plate 34 can further cause the bone plate 34 to compress the bone fragments 22 along the transverse direction T.

The insertion instrument 70 can cause the bone plate 34 to move from the first position 21 to the loaded position 23 in the manner described above. Thus, when the bone plate 34 is in the loaded position 23, the bone fixation member 38 configured as the compression screw 41 can be driven through the cannula 71, through the bone fixation hole 40, and into the underlying bone 26. The compression screw 41 can be driven into the underlying bone 26 until the shaft 66 threadedly purchases with the far cortical wall 30 in the manner described above. As the shaft threadedly purchases with the far cortical wall 30, the unthreaded outer surface 43b of the head 43 of the compression screw 41 abuts the interior surface 60 of the bone fixation hole 40, thereby compressing the bone plate 34 against the underlying bone 26. The insertion instrument 70 can then be disengaged from the bone plate 34 in the manner described above, which allows the bone plate 34 to move from the loaded position 23 to the compression position 25 in the manner described above.

Alternatively, it should be appreciated that the compression screw 41 can alternatively provide the biasing force against the bone plate 34 that causes the bone plate 34 to move from the first position 21 to the loaded position 23. For instance, the compression screw 41 can be driven through the bone fixation hole 40 while the gripper 72 is engaged with the bone plate body 42. In this example, the distal end of the cannula 71 does not apply the biasing force to the bone plate body 42 that causes the bone plate 34 to move to the loaded position 23. Thus, the distal end of the cannula 71 can be in abutment with the bone plate body 42, or can be spaced from the bone plate body 42. As described above, the compression screw 41 is driven into the underlying bone 26 until the head 43 abuts the interior surface 60 of the bone fixation hole 40. Continued rotation of the compression screw 41 causes the head 43 to apply a compressive force to the bone plate 34 in the inward direction 47a. As the bone fixation member 38 applies the compressive force to the bone plate 34 while the gripper 72 is engaged with the bone plate 34, the compressive force biases the bone plate 34 to move from the first position 21 to the loaded position 23. In particular, the gripper 72 can brace the bone plate 34 by applying the counterforce to the bone plate 34 as the bone fixation member 38 applies the biasing force to the bone plate 34. Accordingly, the bone plate 34 can be compressed against the underlying bone 26 simultaneously as the bone plate 34 is moved from the first position to the loaded position. Once the bone plate 34 is compressed against the bone and the bone plate is in the loaded position 23, the insertion instrument 70 can be disengaged from the bone plate 34 in the manner described above so as to allow the bone plate 34 to move from the loaded position 23 to the compression position 25. Further, because the bone fixation member 38 can apply the biasing force to the bone plate 34 that causes the bone plate 34 to move to the loaded position, the insertion instrument 70 can be constructed such that the cannula 71 is stationary with respect to movement along the inward direction 47a relative to the gripper 72.

As described above, the bone plate 34 can be moved from the first position 21 to the loaded position 23 before or after the bone plate 34 has been placed against the underlying bone 26. In one example, the insertion instrument 70 can apply the biasing force to the bone plate 34 that causes the bone plate 34 to move from the first position 21 to the loaded position 23. The insertion instrument 70 can further maintain the biasing force until it is disengaged from the bone plate 34. In another example, the bone plate 34 can be moved from the first position 21 to the loaded position 23 prior to engagement with the insertion instrument 70 in the manner described above. In still another example, the bone fixation member 38 can apply the biasing force to the bone plate 34 that causes the bone plate 34 to move from the first position 21 to the loaded position 23. The bone fixation member 38, in combination with the insertion instrument 70, can maintain the bone plate 34 in the loaded position until the insertion instrument 70 is disengaged from the bone plate 34. It should be appreciated, of course, that the bone plate 34 can be moved from the first position 21 to the loaded position 23 in any suitable manner as desired, such that the bone plate 34 can move to the compression position 25 whereby the bone plate 34 applies compressive forces to the underlying bone fragments 22 as described above.

Referring now to FIGS. 7A-8B, the bone plate described above with respect to FIGS. 1-6C can be constructed in accordance with any suitable alternative embodiment as desired. For instance, the bone plate 34 can be elongate along a length that is oriented along a longitudinal direction L that is substantially perpendicular to the transverse direction T, and a width along a lateral direction A that is substantially perpendicular to each of the longitudinal direction L and the transverse direction T. The bone plate 34 can define at least one end wall 51, such as opposed end walls 51 that are spaced from each other along the longitudinal direction L. The bone plate 34 can further define at least one side wall 59, such as opposed side walls 59 that are opposite each other along the lateral direction A. The side walls 59 can extend from a first one of the end walls 51 to a second one of the end walls 51. The end walls 51 can be parallel with each other or nonparallel as desired. Similarly, the side walls 59 can be parallel with each other. Alternatively, the side walls 59 can be non-parallel with each other as desired. Thus, the end walls 51 and the side walls 59 can combine so as to define the outer perimeter 50 of the bone plate 34. The outer perimeter 50 can define a rectangular shape or any suitable alternative shape as desired, such as circular, oval, round, triangular, square, rectangular, or any suitable shape as desired.

In one example, the bone plate 34 can be substantially planar along a plane defined by the longitudinal direction L and the lateral direction A when the bone plate 34 is in the first position 21. Thus, the bone facing surface 44 and the outer surface 46 can each be oriented along respective planes that are defined by the longitudinal direction L and the lateral direction A. The bone plate 34 can further include the inner apertures 55 and interconnected linkages 56 as described above. The inner apertures 55 can be elongate along a direction that is angularly offset with respect to the longitudinal direction L and the transverse direction T. The end walls 51 can extend continuously and uninterrupted from a first one of the side walls 59 to a second one of the side walls 59. Similarly, the side walls 59 can extend continuously and uninterrupted from a first one of the end walls 51 to a second one of the end walls 51. Alternatively, if desired, the bone plate 34 can further include one or more outer apertures 54 that interrupt one or both of the end walls 51 and the side walls 59. At least some of the linkages 56 can be oriented at an angle with respect to the longitudinal direction L.

Accordingly, the linkages 56 can flex as the bone plate 34 moves from the first position 21 to the loaded position 23. In the first position 21, the bone plate 34 can have a first length L1 along the longitudinal direction L from a first one of the end walls 51 to a second one of the end walls 51. In the loaded position 23, that bone plate can have a second length L2 along the longitudinal direction L from the first one of the end walls 51 to the second one of the end walls 51. The second length L2 can be greater than the first length L1. Because the linkages 56 flex as the bone plate 34 moves from the first position 21 to the loaded position 23, the bone plate body 42 is naturally resilient and biases the bone plate 34 to move from the loaded position 23 toward the first position 21. In particular, the bone plate body 42 can bias the bone plate 34 to move from the loaded position 23 to the compression position 25. The bone plate 34 can be substantially planar as described above when the bone plate 34 is in the loaded position 23. It is recognized, however, that the bone plate 34 can be non-planar when it is placed against the underlying bone (see FIG. 8b) as it can become contoured to the bone fragments 22 when placed against the underlying bone 26. It can be further appreciated that the bone plate 34 can be secured to the underlying bone in the first position, such that the bone plate provides a barrier that maintains the comminuted bone fragments in position to facilitate bone healing.

The bone plate 34 can include a first at least one bone fixation hole 40a that extends from the outer surface 46 to the bone facing surface 44, and a second at least one bone fixation hole 40b that extends from the outer surface to the bone facing surface. The first and second at least one bone fixation holes 40a and 40b can be spaced from each other along the longitudinal direction L. In one example, the first at least one bone fixation hole 40a can include a first pair of bone fixation holes 40a. The first pair of bone fixation holes 40a can be aligned with each other along the lateral direction A. For instance, the first pair of bone fixation holes 40*a* can extend through the first one of the end walls 51. Similarly, the second at least one bone fixation hole 40*b* can include a second pair of bone fixation holes 40*b*. The second pair of bone fixation holes 40*b* can be aligned with each other along the lateral direction A. For instance, the second pair of bone fixation holes 40*b* can extend through the second one of the end walls 51.

As described above with respect to FIGS. 1-6C, one or more up to all of the respective interior surfaces 60 that define the bone fixation holes 40*a* and 40*b* can be unthreaded, and thus configured to receive a compression screw 41. Alternatively or additionally, as illustrated in FIG. 9, one or more up to all of the interior surfaces 60 of the bone fixation holes 40*a* and 40*b* can be threaded and configured to threadedly mate with the head 43 of a locking screw 39 as described above (see FIGS. 2B-2C). Alternatively still or additionally still, as illustrated in FIG. 10, one or more up to all of the bone fixation holes 40*a* and 40*b* can be configured as variable angle screw holes 45 as described above (see FIGS. 4B-4C).

Figure 8A:
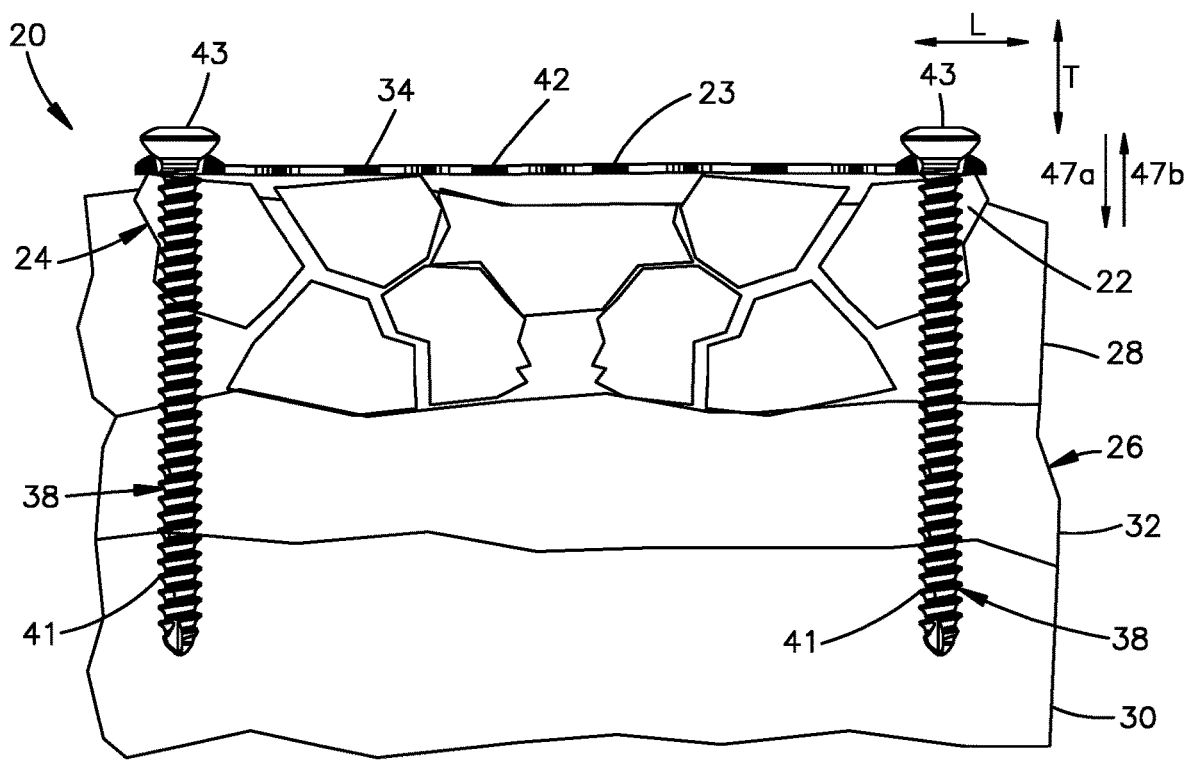
FIG. 8A is a sectional side elevation view of a bone fixation system including the bone plate illustrated in FIG. 7C and a plurality of bone fixation members inserted through the bone plate and fixed to the underlying bone.
Figure 8B:
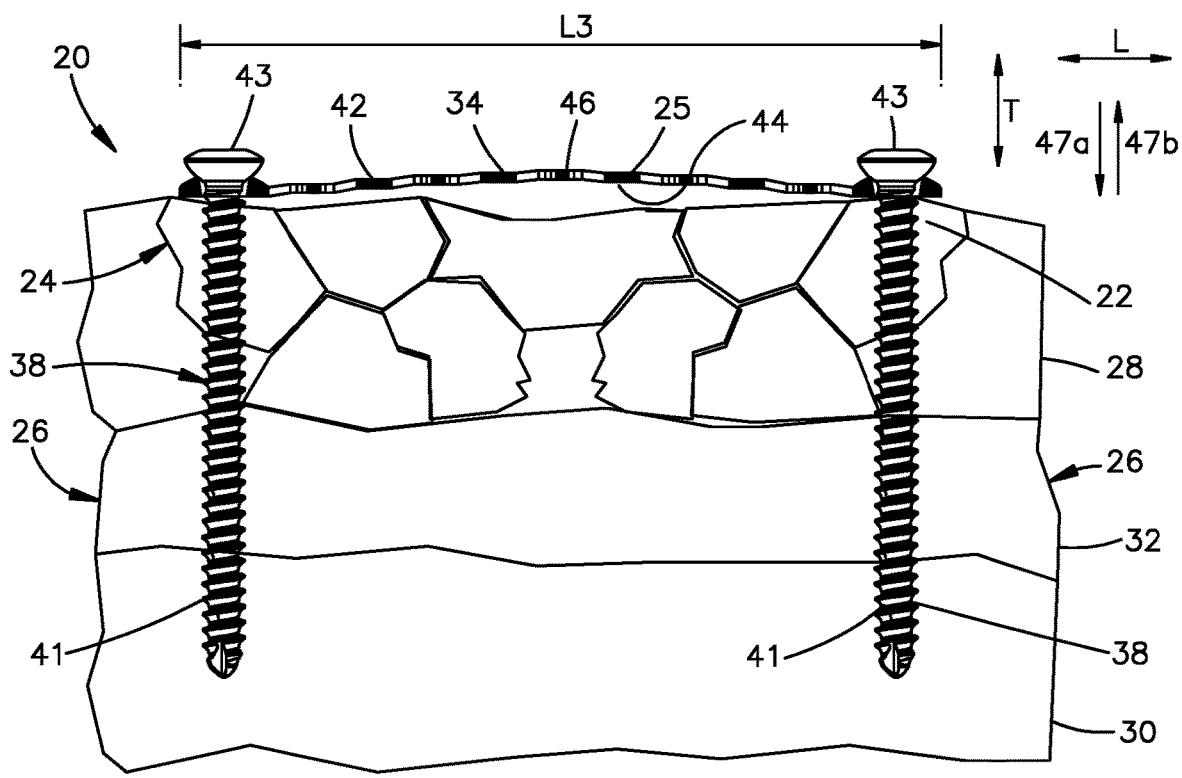
FIG. 8B is a sectional side elevation view of the bone fixation system illustrated in FIG. 8A, but showing the bone having moved from the loaded position to a compression position having a third length that is greater than the first length and less than the second length.

Referring now to FIGS. 8A-8B, the bone plate 34 can be moved from the first position 21 to the loaded position 23, and the bone fixation members 38 can be driven through respective ones of the bone fixation holes 40*a* and 40*b* and into the underlying bone 26 in any manner as described above. In particular, the gripper arms 75 (see FIG. 3A-3D) can engage the end walls 51 and move away from each other along the longitudinal direction L, thereby applying the biasing force to the bone plate 34 that increases the length of the bone plate 34 from L1 to L2. In another example, the bone plate 34 can be made from Nitinol, and cooled in the loaded position.

Thus, when the bone plate 34 is in the loaded position 23 and placed against the underlying bone 26, the bone fixation members 38 can be driven through respective ones of the bone fixation holes 40*a* and 40*b* and into the underlying bone 26. The biasing force maintaining the bone plate in the loaded position can then be removed. Alternatively or additionally, when the bone plate 34 is made from Nitinol, the temperature of the bone plate 34 can be raised to the heated temperature as descried above. Once the bone fixation members 38 have engaged the respective interior surfaces 60 and the far cortical wall 30, the bone plate body 42 can bias the bone plate 34 to move from the loaded position 23 to the compression position 25. Because the bone plate 34 is naturally biased to decrease its length along the longitudinal direction L when in the compression position 25, the first pair of bone fixation holes 40*a* and the second pair of bone fixation holes 40*b* can be biased to move toward each other along the longitudinal direction L. Accordingly, the corresponding bone fixation members 38 can compress the bone fragments 22 toward each other along the longitudinal direction L. The bone plate 34 can be sized such that the bone plate spans the comminuted fracture, such that the bone fixation holes 40*a* and 40*b* are aligned with bone that is suitable for purchase with the bone fixation members 38. Thus, the bone fixation members 38 can be driven through respective ones of the bone fixation holes 40*a* and 40*b* and purchase into respective first and second regions the underlying bone that are separated from each other by the comminuted fracture. The bone fixation members 38 can be driven into the bone fixation holes 40*a* and 40*b* when the bone plate 34 is in the loaded position as described above. Alternatively, the bone fixation members 38 can be driven into the bone fixation holes 40*a* and 40*b* when the bone plate 34 is in the first position.

Further, when the bone plate 34 is placed against the bone, the flexibility of the bone plate body 42 can cause the bone plate 34 to become contoured to the underlying bone 26. Thus, the ends 51 can be offset from a central location of the bone plate 34 along the inward direction 47*a*. The contour can be increased when the bone fixation members 38 are configured as compression screws 41 that compress the bone plate 34 against the underlying bone 26. As a result, when the bone plate 34 is in the compression position 25, the end walls 51 can apply a compression force against the bone fragments 22 that are disposed within the footprint of the bone plate 34. When the bone plate 34 is in the compression position 25, the bone plate 34 can define a third length L3 that is between the first length L1 and the second length L2. The resulting compression force applied by the bone plate 34 to the bone fragments 22 can reduce or remove the gaps between the bone fragments 22 such that the bone fragments 22 contact each other, thereby improving bone healing. It should be appreciated that the bone plate 34 described in FIGS. 1-6C can further be elongate along the longitudinal direction L as described with respect to FIGS. 7A-8B.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

What is claimed:

1. A bone plate comprising:
   a bone plate body that defines an outer surface and a bone facing surface opposite the outer surface in an inward direction, and the bone plate further including a bone screw hole that extends through the bone plate body from the outer surface to the bone facing surface,
   wherein the bone plate is movable from a first position to a loaded position, and the bone plate is further biased to iterate from the loaded position toward the first position, such that when the bone plate is in a compression position between the first position and the loaded position, the bone plate is configured to apply a compressive forced against an underlying bone, and
   wherein the bone plate body defines an outer perimeter and a central location, a plurality of petals that extend radially out from the central location, and at least one aperture disposed circumferentially between adjacent ones of the petals, wherein each of the petals is configured to apply a radially inward compressive force to bone fragments of the underlying bone when the bone plate is moved from the loaded position to the compression position.

2. The bone plate as recited in claim 1, wherein the bone plate is flatter in the loaded position than in the compression position.

3. The bone plate as recited in claim 1, wherein the outer perimeter is biased in the inward direction with toward to the central location as the bone plate iterates from the loaded position to the compression position.

4. The bone plate as recited in claim 3, wherein the bone plate body comprises at least one aperture that extends through the bone plate body from the outer surface to the bone facing surface, and wherein the at least one aperture is open to the outer perimeter of the bone plate body.

5. The bone plate as recited in claim 1, wherein the bone plate body is resilient and naturally biases the bone plate to the compression position from the loaded position.

6. The bone plate as recited in claim 1, wherein the bone plate body naturally biases the bone plate from the loaded position to the compression position in response to an application of heat to the bone plate body.

7. The bone plate as recited in claim 1, wherein the bone plate body is resilient along a direction substantially perpendicular to the inward direction, such that movement of portion of the bone plate body away from the bone screw hole in the direction causes the bone plate body to naturally bias the portion of the bone plate body toward the bone screw hole.

8. A bone fixation system comprising:
the bone plate as recited in claim 1; and
a bone screw sized to be inserted through the bone screw hole in the inward direction, the bone screw having a screw head and a screw shaft having an outer shaft surface, wherein at least a portion of the outer shaft surface is threaded.

9. The bone fixation system as recited in claim 8, further comprising an insertion instrument having a cannula configured to receive the bone screw and direct the bone screw toward the bone screw hole.

10. The bone fixation system as recited in claim 9, wherein the insertion instrument defines an engagement surface that at least partially surrounds an opening to the bone screw hole, the opening disposed at the outer surface.

11. The bone fixation system as recited in claim 9, wherein the insertion instrument comprises a gripper spaced from the engagement surface along a direction perpendicular to the transverse direction, the gripper configured to engage the bone plate body.

12. The bone fixation system as recited in claim 11, wherein the bone plate body is configured to receive a force in the inward direction, and the gripper is configured to apply a counterforce to the bone plate body in an outward direction opposite the inward direction as the bone plate is biased from the first position to the loaded position.

13. The bone fixation system as recited in claim 12, wherein the gripper is configured to grip an outer perimeter of the bone plate body so as to provide the counterforce.

14. The bone fixation system as recited in claim 12, wherein the bone screw is configured to provide the force to the bone plate body.

15. The bone fixation system as recited in claim 12, wherein the insertion instrument is configured to provide the force to the plate body.

16. The bone fixation system as recited in claim 15, wherein the insertion instrument defines an engagement surface that is configured to abut the outer surface of the plate body at a location adjacent the bone screw hole, and the engagement surface is configured to provide the force.

17. The bone fixation system as recited in claim 16, wherein the engagement surface is movable relative to the gripper in the inward direction so as to move the plate from a first position to the loaded position.

18. The bone fixation system as recited in claim 16, wherein the gripper is movable relative to the engagement surface in the outward direction so as to move the plate from the first position to the loaded position.

19. The bone plate as recited in claim 1, wherein the bone screw hole extends along a central axis that defines a centerline that passes through a geometric center of the bone plate body.

* * * * *